US006326020B1

(12) United States Patent
Kohane et al.

(10) Patent No.: US 6,326,020 B1
(45) Date of Patent: Dec. 4, 2001

(54) LOCAL ANESTHETIC FORMULATIONS

(75) Inventors: Daniel S. Kohane, Newton; Charles B. Berde, Brookline; Gary Strichartz, Sherborn; Robert S. Langer, Newton, all of MA (US)

(73) Assignees: Children's Medical Center Corporation; Brigham and Women's Hospital, both of Boston, MA (US)

( * ) Notice: Subject to any disclaimer, the term of this patent is extended or adjusted under 35 U.S.C. 154(b) by 0 days.

(21) Appl. No.: 09/079,622

(22) Filed: May 15, 1998

Related U.S. Application Data

(60) Provisional application No. 60/046,761, filed on May 16, 1997, provisional application No. 60/046,163, filed on May 16, 1997, provisional application No. 60/046,683, filed on May 16, 1997, and provisional application No. 60/053,462, filed on Jul. 23, 1997.

(51) Int. Cl.[7] .......... A61F 2/00
(52) U.S. Cl. .......... 424/426
(58) Field of Search .......... 424/451, 501, 424/489, 499, 422, 426, 497

(56) References Cited

U.S. PATENT DOCUMENTS

| | | | |
|---|---|---|---|
| 3,957,996 | 5/1976 | Adams et al. . | |
| 3,966,934 | 6/1976 | Adams et al. . | |
| 4,001,413 | 1/1977 | Adams et al. . | |
| 4,022,899 * | 5/1977 | Adams et al. | 424/251 |
| 4,029,793 | 6/1977 | Adams et al. . | |
| 4,029,794 | 6/1977 | Adams et al. . | |
| 4,313,958 | 2/1982 | LaHann . | |
| 4,401,663 | 8/1983 | Buckwalter et al. . | |
| 4,443,473 | 4/1984 | Buckwalter et al. . | |
| 4,460,602 | 7/1984 | Buckwalter . | |
| 4,493,848 | 1/1985 | LaHann et al. . | |

(List continued on next page.)

FOREIGN PATENT DOCUMENTS

| | | |
|---|---|---|
| 776 769 A1 | 12/1971 | (BE) . |
| 750 909 | 1/1997 | (EP) . |
| WO 94/01166 A1 | 1/1994 | (WO) . |
| WO 94/05265 | 3/1994 | (WO) . |
| WO 96/41616 | 12/1996 | (WO) . |

OTHER PUBLICATIONS

Kao, "Tetrodotoxin, saxitoxin and their significance in the study of excitation phenomena," *Pharmacological Reviews*, vol. 18 (2) pp. 999–1049 (1966).

(List continued on next page.)

*Primary Examiner*—Thurman K. Page
*Assistant Examiner*—R. Joynes
(74) *Attorney, Agent, or Firm*—Holland & Knight LLP

(57) ABSTRACT

Combinations of naturally occurring site 1 sodium channel blockers, such as tetrodotoxin (TTX), saxitoxin (STX), decarbamoyl saxitoxin, and neosaxitoxin (referred to jointly herein as "toxins"), with other agents, have been developed to give long duration block with improved features, including safety and specificity. In one embodiment, duration of block is greatly prolonged by combining a toxin with a local anesthetic, vasoconstrictor, glucocorticoid, and/or adrenergic drugs, both alpha agonists (epinephrine, phenylephrine), beta-blockers (propranalol), and mixed central-peripheral alpha-2 agonists (clonidine), or other agents. In another embodiment, the duration of nerve block from toxin can be greatly enhanced by the inclusion of amphiphilic or lipophilic solvents. In still another embodiment, the effectiveness of these compositions is enhanced by microencapsulation within polymeric carriers, preferably biodegradable synthetic polymeric carriers. Modality specific nerve block can be obtained using combinations of toxin with vanilloids.

23 Claims, 7 Drawing Sheets

U.S. PATENT DOCUMENTS

| | | | | |
|---|---|---|---|---|
| 4,544,668 | | 10/1985 | Janusz et al. . | |
| 4,544,669 | | 10/1985 | LaHann et al. . | |
| 4,564,633 | | 1/1986 | LaHann et al. . | |
| 4,997,853 | | 3/1991 | Bernstein . | |
| 5,008,289 | | 4/1991 | Bernstein . | |
| 5,013,759 | | 5/1991 | Berman et al. . | |
| 5,045,565 | | 9/1991 | Gardner et al. . | |
| 5,099,030 | | 3/1992 | Gardner et al. . | |
| 5,134,166 | | 7/1992 | Bernstein . | |
| 5,618,563 | * | 4/1997 | Berde et al. ......................... | 424/501 |

OTHER PUBLICATIONS

Olivera et al., "Diversity of Conus Neuropeptides," *Science*, 249:257–263, (1990).

Schneider, et al., "A preferential inhibition of impulses in C–fibers of the rabbit vagus nerve by veratridine, an activator of sodium channels," *Anesthesiology* 74:270–281 (1991).

Thalhammer et al., "Neurologic evaluation of the rat during sciatic nerve block with Iidocaine," *Anesthesiology* 82(4): 1013–1025 (1995).

Wagner, et al., "Salitoxin and Procaine Act Independently on Separate Sites of the Sodium Channel," *Pflugers Arch*. 364: 65–70 (1976).

* cited by examiner

LOCAL ANESTHETIC FORMULATIONS

This application is a provisional of application Nos. 60/046,761, filed May 16, 1997, and Ser. No. 60/046,163, filed May 16, 1997, Ser. No. 60/046,683, filed May 16, 1997 and Ser. No. 60/053,462, filed Jul. 23, 1997.

FIELD OF THE INVENTION

The present invention relates to formulations or methods that provide prolonged local anesthesia with an enhanced margin of safety based on the combination of site 1 sodium channel blockers, and agents such as vasoconstrictors, local anesthetics, vanilloid receptor agonists and/or corticosteroids, lipophilic or amphiphilic solvents, and microparticulate formulations thereof.

BACKGROUND OF THE INVENTION

Currently used amino ester and amino amide local anesthetics have limited duration of action, too short to relieve most postoperative pain, and low potency, requiring millimolar concentrations for effectiveness. These compounds only produce local anesthesia lasting for short periods and therefore require repeated administration or catheter infusions if clinical effect is desired for periods of longer than 4 to 6 hours. The commonly used local anesthetics of the amino-amide and amino-ester classes are of relatively low potency, in that they are administered in the mg/kg range in vivo, and they have blocking concentrations in isolated nerve ranging from 10 mM to 1 mM. There is also the risk of systemic toxicity, evidenced by seizures and cardiac arrythmias, the risk of local nerve toxicity, meaning that high concentrations of current-day local anesthetics can damage nerves and muscles, which is a significant clinical problem with spinal anesthesia with lidocaine. There is also a lack of modality-selectivity, resulting in numbness and low blood pressure along with pain relief.

It has been a long standing goal to obtain local anesthetic formulations enhancing or prolonging nerve blockade with minimal side effects. A number of naturally occurring toxins have much greater intrinsic potency, with concentrations of as low as $10^{-7}$ to $10^{-8}$ M being effective to block conduction of nerve impulses. However, tetrodotoxin systemic toxicity, like that of other local anesthetics, can result in diaphragmatic paralysis leading to respiratory arrest and death. Hypotension, presumably due to smooth muscle relaxation and/or vasomotor nerve blockade, is also a prominent feature. Tetrodotoxin is safer than conventional local anesthetics in a hospital setting with the availability of respiratory support, in that cardiotoxicity is relatively minimal, and tetrodotoxin does not cause seizures. Clinically, the toxic syndrome is similar to curare poisoning.

The site 1 toxins by themselves have too much uptake into the systemic circulation and too little local action to be effective. In the mid-1970s, Adams et al. reported that toxins such as tetrodotoxin and saxitoxin could be combined with local anesthetics to prolong local anesthesia. See U.S. Pat. Nos. 3,966,934, 3,957,996, 4,001,413, 4,029,794, 4,029,793, and 4,022,899 to Adams, et al. Better results were obtained with inclusion of epinephrine. This technology was never developed clinically, however. Published data did not clearly demonstrate nociceptive block, measured as loss of pain sensation. Blockade was simply defined as loss of motor function in the injected limb. The possibility that systemic toxicity was the cause of the observed nerve blocks was also not assessed. The addition of a vasoconstrictor to slow systemic absorption was shown to reduce toxicity and decrease mortality, but neither effect was quantified. Subsequent studies have confirmed that the observations by Adams, et al. were in fact due largely to systemic TTX toxicity (generalized weakness and numbness, and perhaps low blood pressure), not due to local nerve blockade, as they thought.

Other attempts to prolong nerve blockade have involved the use of polymeric formulations providing controlled release of local anesthetics, alone or in combination with a glucocorticoid. For example, U.S. Pat. No. 5,618,563 to Berde and Linger describes biodegradable polymer matrices for sustained release of local anesthetic agents. Dexamethasone was included to avoid inflammation due to the polymer, and was found to increase substantially the period of nerve blockade so that relief could be obtained for periods as long as a few days. There are many disadvantages, however, to the use of the polymeric microparticles, including difficulties in obtaining good suspensions for injection, the need to use a large gauge needle for delivery, polymer residual, and potential risk of infection.

It is therefore an object of this invention to provide improved long acting local anesthetic formulations to provide more prolonged nerve blockade, which is safe, efficacious, and easy to administer.

It is another object of this invention to provide formulations providing modality specific nerve blockade.

SUMMARY OF THE INVENTION

Combinations of naturally occurring site 1 sodium channel blockers, such as tetrodotoxin (TTX), saxitoxin (STX), decarbamoyl saxitoxin, and neosaxitoxin (referred to jointly herein as "toxins"), with other agents, have been developed to give long duration block with improved features, including safety and specificity.

In one embodiment, duration of block is greatly prolonged by combining a toxin with a local anesthetic, vasoconstrictor, glucocorticoid, and/or adrenergic drugs, both alpha agonists (epinephrine, phenylephrine), beta-blockers (propranalol), and mixed central-peripheral alpha-2 agonists (clonidine), or other agents.

Modality specific nerve block can be obtained using combinations of toxin with vanilloids.

In another embodiment, the duration of nerve block from toxin can be greatly enhanced by the inclusion of amphiphilic or lipophilic solvents.

In still another embodiment, the effectiveness of these compositions is enhanced by microencapsulation within polymeric carriers, preferably biodegradable synthetic polymeric carriers. As demonstrated by the examples, providing these formulations as microparticulate compositions yields even longer lasting local anesthesia than that obtained with toxin or local anesthesia in solution.

μg) alone (open squares), 15.4 mM (0.5%) bupivacaine alone (open circles) with 30 μM TTX (3 μg) in combination with bupivacaine (dark circles); 30 μM TTX (3 μg) in combination with 55 μm (1:100,000) epinephrine (dark squares); 30 μM TTX (3 μg) in combination with both bupivacaine and epinephrine (dark triangles). The dotted line is a line of identify between nociceptive and motor blockade.

Figure 3:
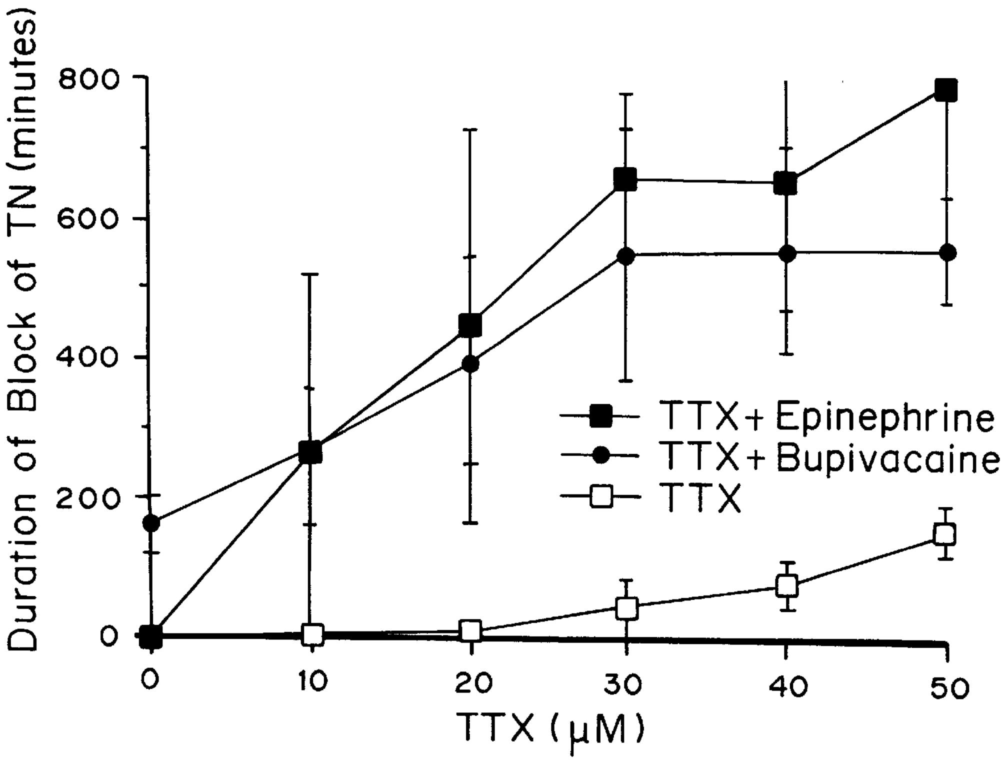

FIG. 3 is a graph comparing the duration of effective block of thermal nociception for various concentrations of TTX alone (open squares) or in combination with 55 μM (1:100,000) epinephrine (dark squares) or 15.4 Mm (0.5%) bupivacaine (dark circles).

Figure 4:
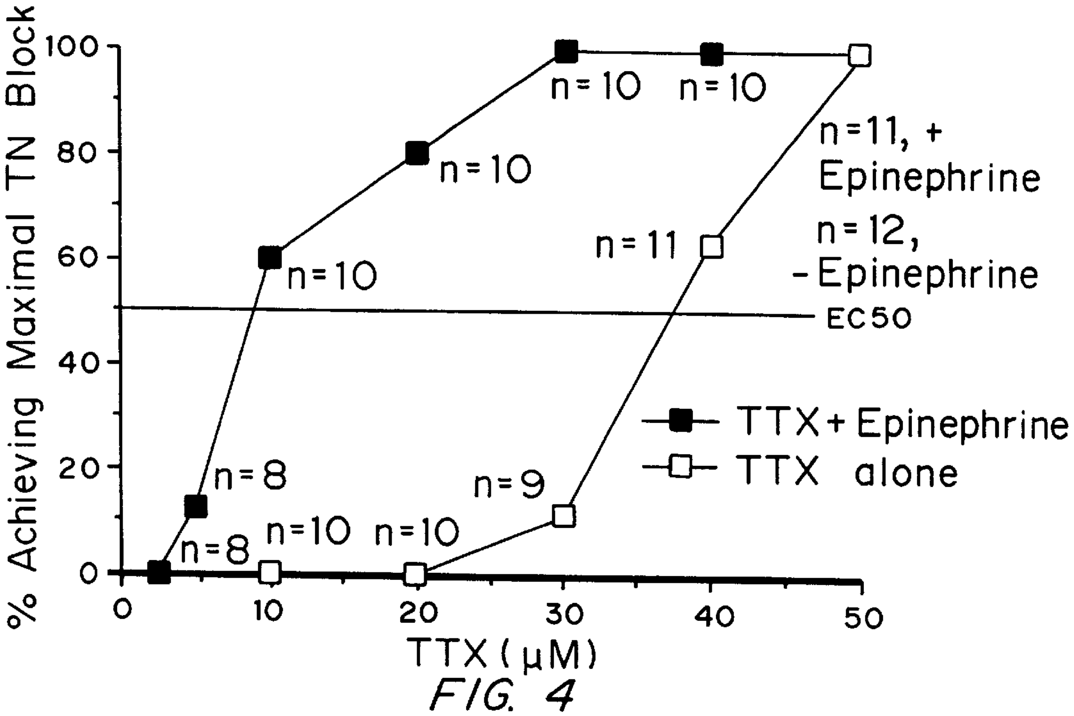

FIG. 4 is a graph of percent achieving maximal TN block versus concentration of TTX (micromolar), to determine $EC_{50}$ (to achieve a maximal thermal nociceptive block, ie. a thermal latency of 12 seconds) for TTX, alone (open squares) or with 55 μM (1:100,000) epinephrine (closed squares), in the injected leg. The $EC_{50}$S for TTX with epinephrine and TTX alone were 11.5 μM and 37.6 μM respectively ($p<0.0001$).

Figure 5:
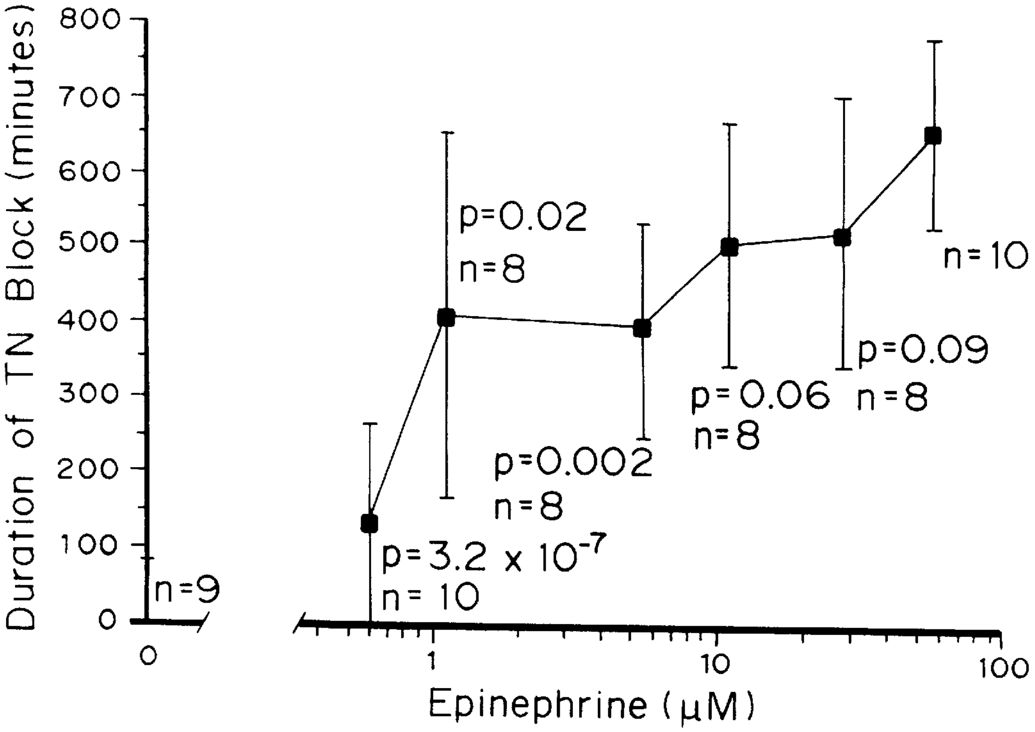

FIG. 5 is a graph of the duration of TN block (minutes) versus concentration of epinephrine (micromolar), showing the effect of epinephrine concentration on the duration of effective block for thermal nociception (DEB-TN) from 3 μg of TTX. 55 μM=1:100,000 epinephrine. Values of DEB-TN are mean±SD. The p values result from t-tests comparing the DEB-TN of TTX with various epinephrine concentrations to TTX with 0.55 mM epinephrine. Epinephrine concentrations as low as 1.1 μm (1:5,000,000) prolonged the DEB-TN.

Figure 6:
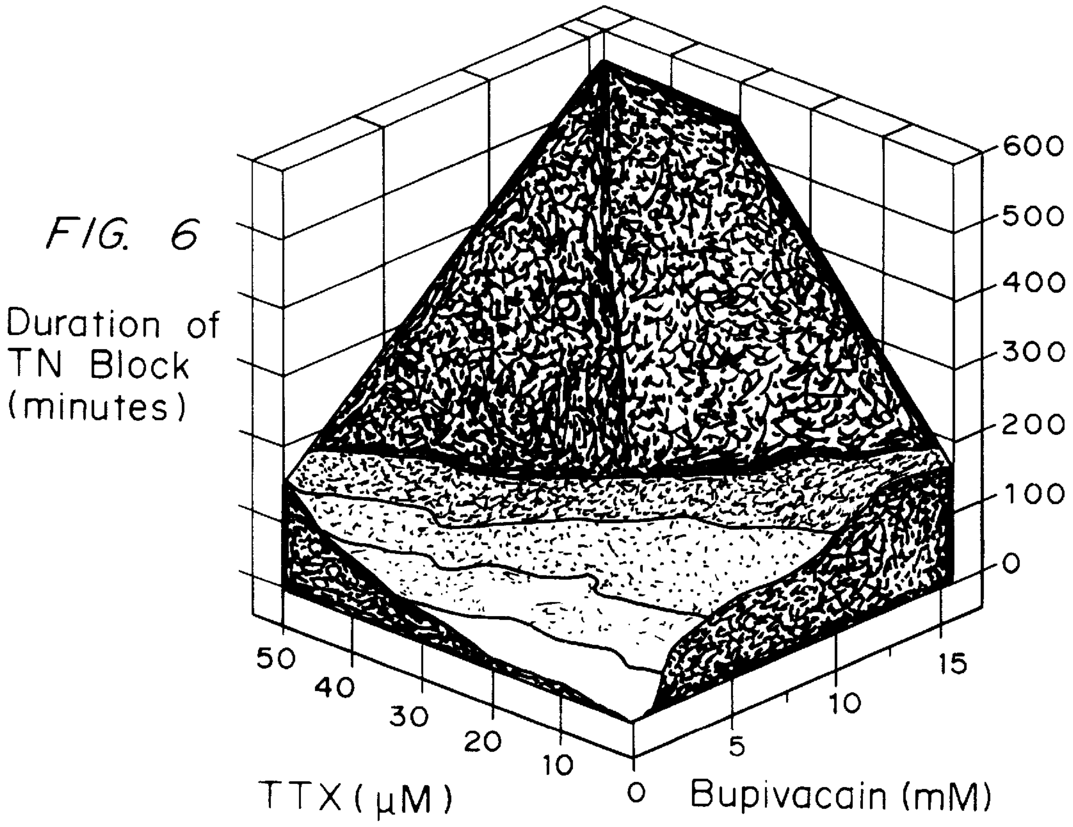

FIG. 6 is a graph showing the duration of effective block of thermal nociception obtained from combinations of various concentrations of bupivacaine and TTX, as well as either drug alone. Each gradation on the surface represents an increment of 50 minutes. The ridge on the leftward face of the surface demonstrates a plateau at bupivacaine dosages above 11.6 mM which is not obvious in this perspective. The thick contour line connecting the DEB-TN for 50 μM TTX and 15.4 mM (0.5%) bupivacaine intersects the DEB-TN achieved by three combinations which should yield equal DEBs (=160 min.) if TTX and bupivacaine were merely additive. The dotted lines demarcate the DEB-TN resulting from one-half the maximal dose of either drug alone.

Figure 7:
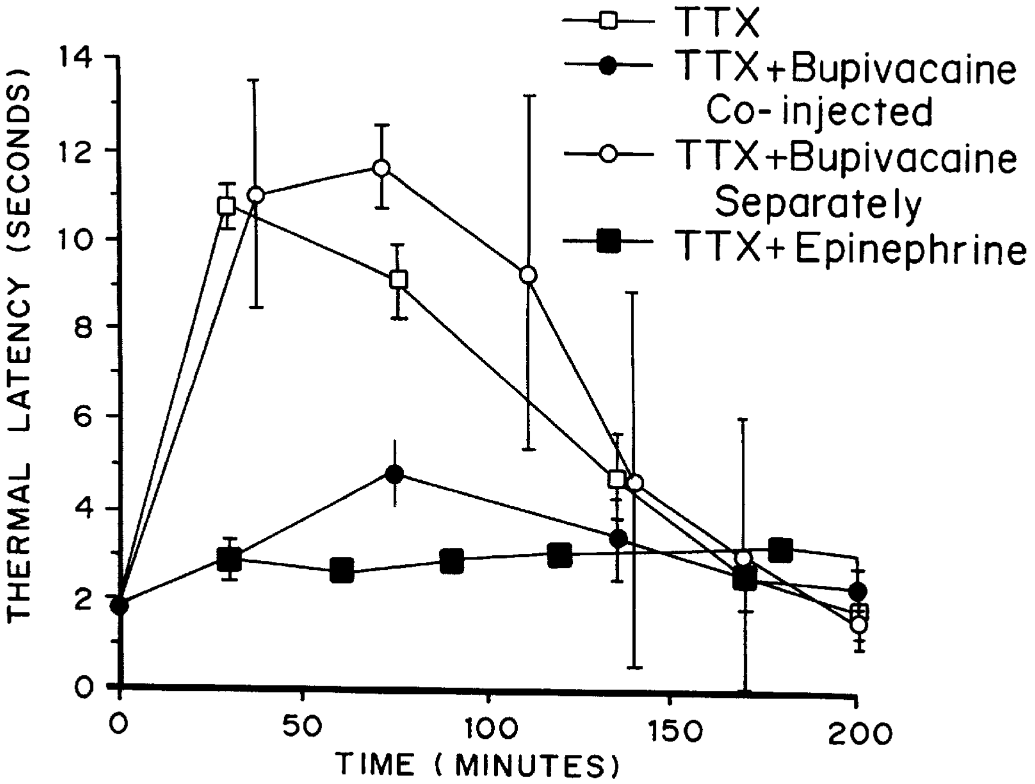

FIG. 7 is a graph comparing thermal latency in the left leg resulting from subcutaneous drug injections at the nuchal midline. 35 mmoles•$kg^{-1}$(11.4 μg/kg) of TTX were injected alone (open squares), or co-injected in 15.4 nM (0.5%) bupivacaine (dark circles), or with bupivacaine injected simultaneously at a separate site (dark triangles). Thermal latency is increased when bupivacaine is not co-injected with TTX. Co-injection of 55 μM (1:100,000) epinephrine has a similar effect on the latency time course of TTX (dark squares). Mean±SD. n=6 for all groups.

Figure 8:
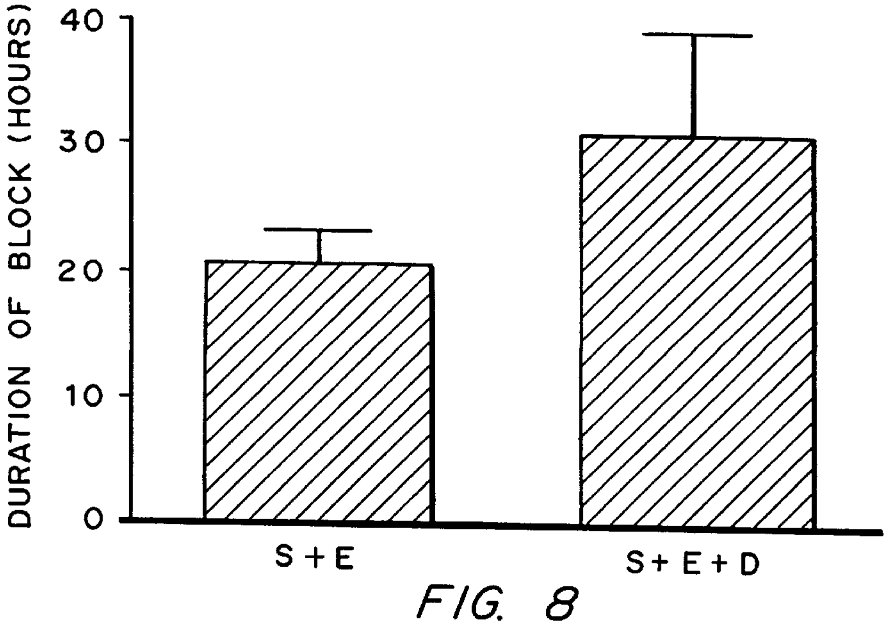

FIG. 8 is a graph comparing the duration (hours) of sciatic nerve block between a preparation of STX plus epinephrine versus STX plus epinephrine plus dexamethasone. The plot shows a clear prolongation of block by addition of dexamethasone.

Figure 9:
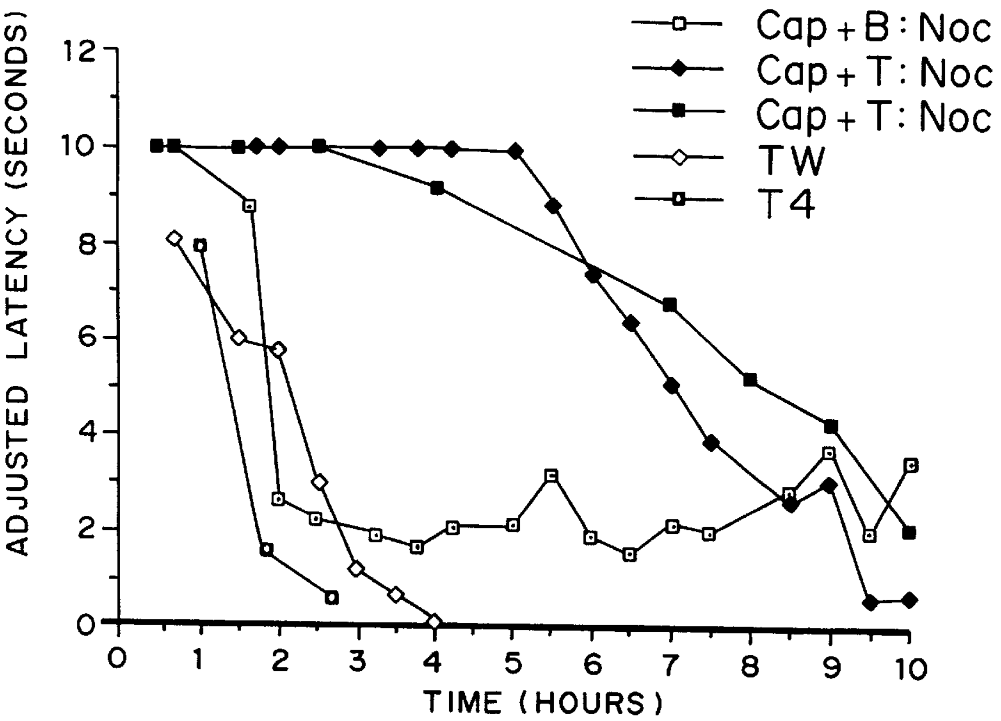

FIG. 9 is a graph of adjusted latency (seconds) over time (hours) following administration of 4 μg of TTX ("T4"); 4 μg of TTX in combination with bupivacaine ("Cap+ B:Noc"); 4 μg of TTX in combination with 30 μg of capsaicin ("Cap+T: Noci I and II"); and 4 μg of TTX in the Tween™ 80 carrier ("TW"). Noci refers to thermal nociception.

Figure 10:
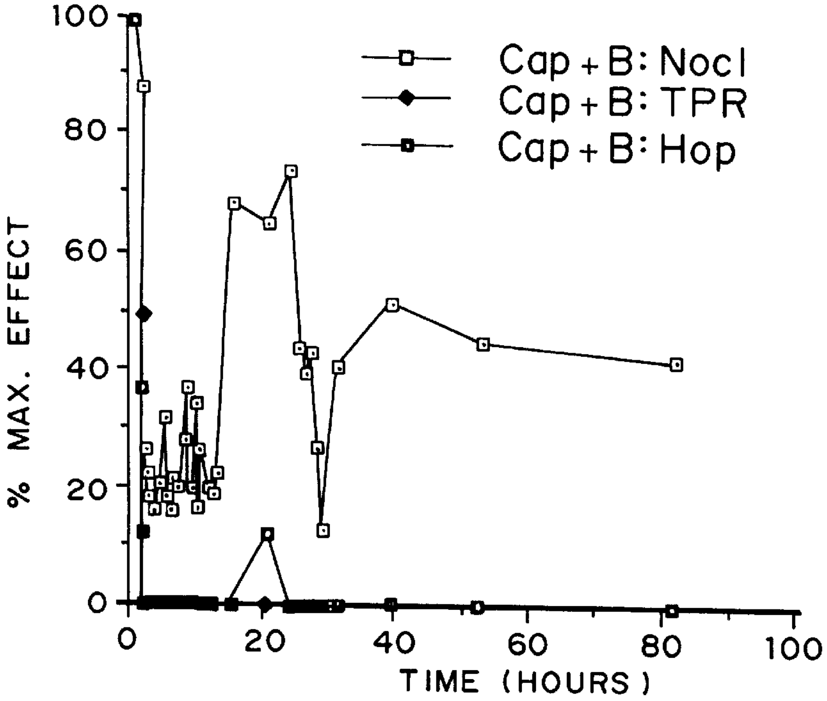

FIG. 10 is a graph of the effect on hotplate latency, measured as percentage of the maximum effect, of 4 μg of TTX in saline ("T4"), 4 μg of TTX in a Tween™-containing carrier ("TW"), 4 μg of TTX with 30 μg of capsaicin (both "Cap+T" curves), and 0.125% bupivacaine with 30 μg of capsaicin ("Cap+B"). n=11 for T4, n=4 for all others. FIG. 10 is a graph comparing the effect of 30 μg of capsaicin in 0.125% bupivacaine on thermal nociception (Noci), tactile placing response (TPR; a measure of proprioceptive and motor function), and ability to hop (Hop).

Figure 11:
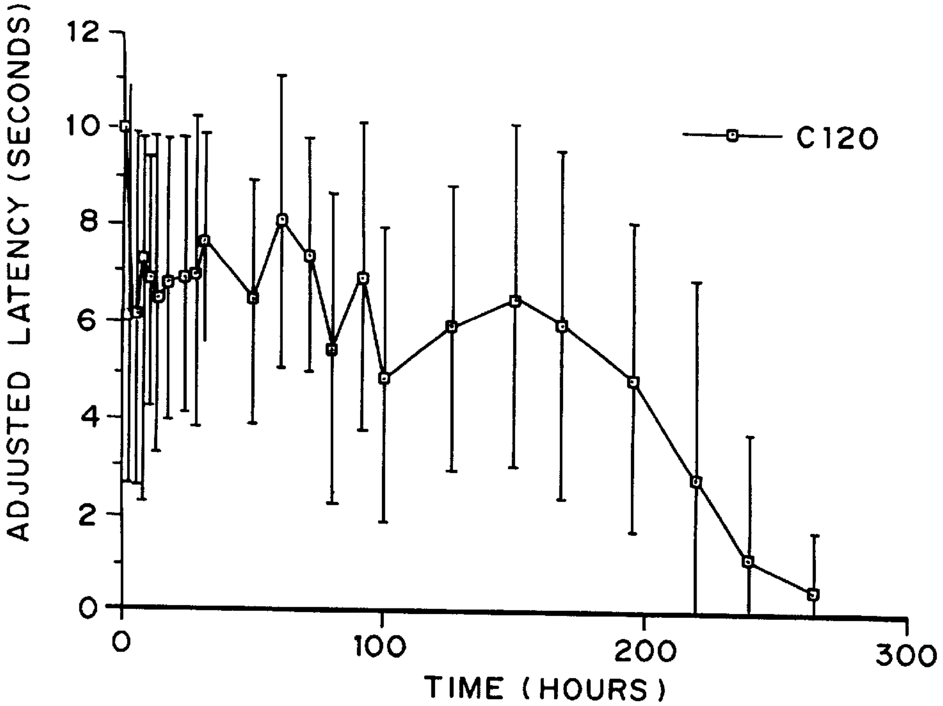

FIG. 11 is a graph of the time course (hours) of the effect of 30 μg of capsaicin in 0.125% BPV on thermal nociception (adjusted latency, seconds) over a ten-day period.

Figure 12:
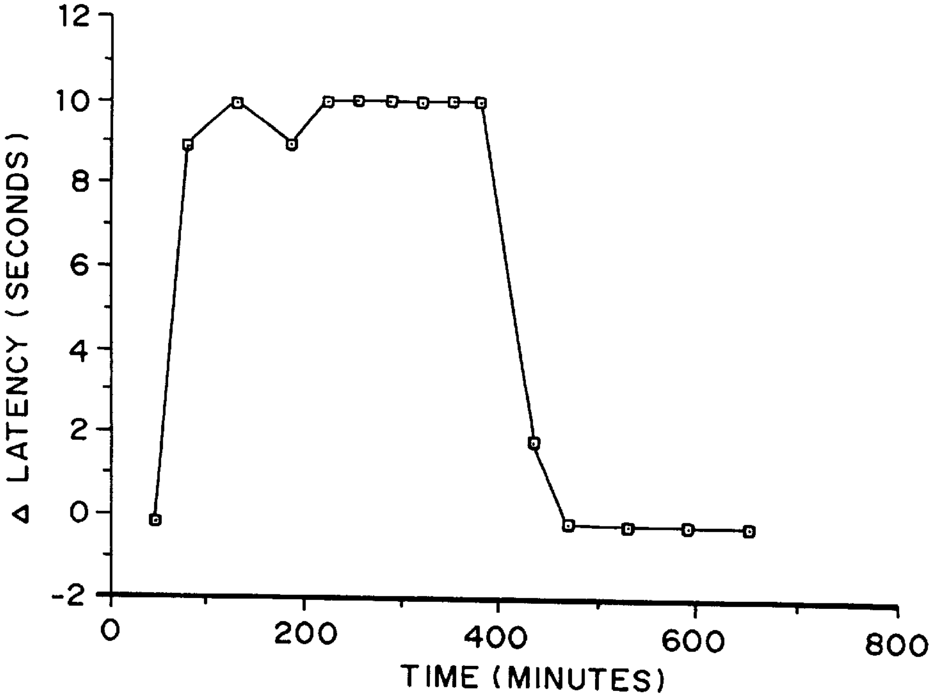

FIG. 12 is a graph of the effect of less than 30 mg (a very small amount) of microspheres containing TTX alone on hotplate latency over time in minutes. The suspending medium contained epinephrine 1:100,000.

Figure 13:
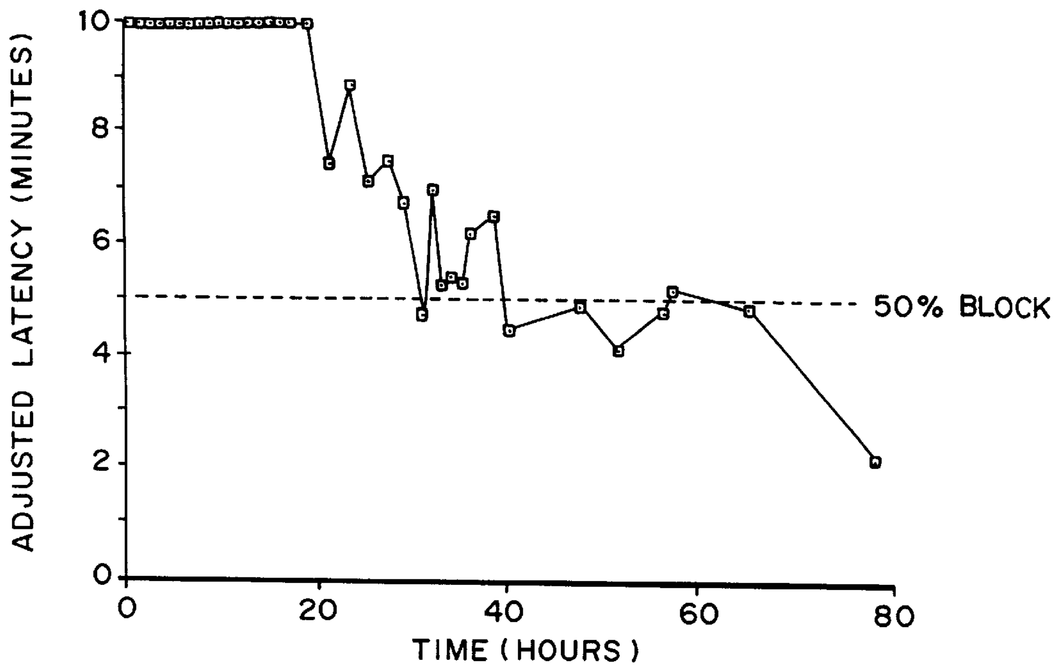

FIG. 13 is a graph of the effect of microspheres containing TTX with bupivacaine on hotplate latency (seconds). The suspending medium contained epinephrine 1:100,000.

Figure 14:
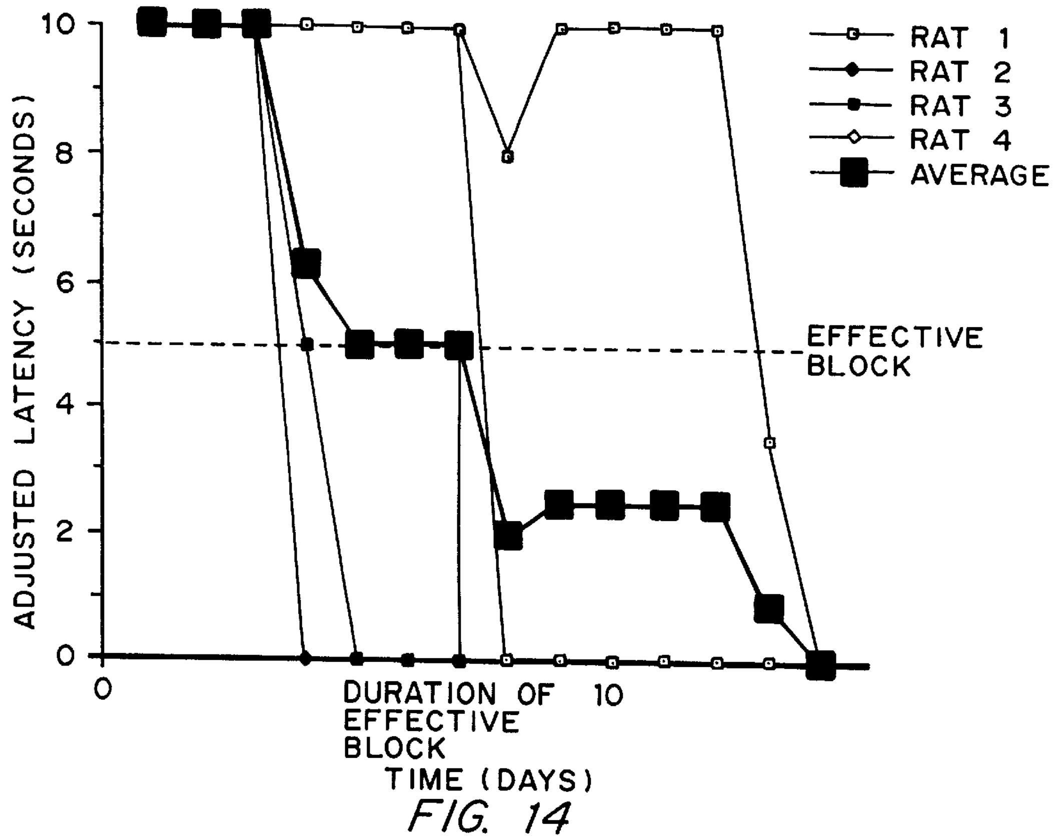

FIG. 14 is a graph of the effect of microspheres containing TTX, bupivacaine, and dexamethasone on hotplate latency. The suspending medium contained epinephrine 1:100,000.

DETAILED DESCRIPTION OF THE INVENTION

Site 1 channel blockers, or toxins, have markedly improved effectiveness, markedly prolonged duration, and reduced systemic toxicity when combined with adrenergic drugs, both alpha agonists (epinephrine, phenylephrine), beta-blockers (propranalol), and mixed central-peripheral alpha-2 agonists (clonidine), or other agents such as vasoconstrictors, glucocorticoids, or vanilloids, as described herein. Preferred toxins are tetrodotoxin and saxitoxin and structurally homologous compounds, such as neosaxitoxin, decarbamoyl saxitoxin, which bind to site I on the sodium channel of nerve cells. Preferred vasoconstrictors are epinephrine and phenylepinephrine, which act on alpha adrenergic receptors. The examples demonstrate that in the correct proportions, Tetrodotoxin (TTX) in combination with epinephrine or with local anesthetics provides a sciatic nerve block that lasts over 10 hours in a rat, which is more than three fold longer duration than can be achieved by any of the local anesthetics currently in clinical use. Durations of block in excess of 20 hours can similarly be obtained with saxitoxin (STX) in combination with epinephrine. This can be extrapolated to an even longer blockade with less toxicity when these preparations are used in larger animals (e.g., humans). This is a liquid preparation, and therefore can be delivered through very small needles. Toxicity is minimal. In the correct proportions, Tetrodotoxin with Bupivacaine and Epinephrine provides a nerve block that lasts roughly 13 hours. Its advantages are similar to those of tetrodotoxin with epinephrine.

As demonstrated by the examples, the combination of a vanilloid (either capsaicin or resiniferotoxin) with site 1 toxins (either TTX or STX) produces a markedly synergistic nerve block, and the nerve block from these combinations is more sensory-predominant than nerve block produced by toxin (TTX) alone, local anesthetic (bupivacaine), and toxin-local anesthetic (TTX-bupivacaine) combinations.

Neither vanilloids nor site 1 toxins produce the cardiac or convulsive systemic toxicities of existing local anesthetics. Thus, combinations of site 1 toxins and vanilloids afford a way of providing prolonged nerve block with better sensory selectivity, markedly reduced risk of convulsions and arrythmias, extremely high potency on a mass basis (micrograms of each drug in rats, projected to be less than 1 to 5 mg of each drug in humans for a 2 to 5 day block).

Site 1 toxins also have markedly improved effectiveness and prolonged duration, and no local toxicity, when combined with FDA-approved amphiphilic vehicles, including non-ionic detergents such as Tween-80, in concentrations of Tween ranging from 0.3%–3%. These solvents, which include alcohols such as ethanol, polyoxyethylene sorbitan derivatives such as Tween, dimethylsulfoxide (DMSO) and others, appear to improve entry of toxin into the nerve. Examples demonstrate prolongation of local anesthesia by coadministration of tetrodotoxin with 1% Tween-20 and 1% ethanol or 3% Tween-80.

The site 1 toxins do not cause local injury to muscle and nerve, unlike existing local anesthetics. This means that prolonged or continuous spinal use and sustained-release local use (as from microspheres) causes less local nerve and muscle injury or inflammation than prolonged spinal administration of local anesthetics or prolonged peripheral nerve blockade from local anesthetic-polymer microspheres. Site 1 toxin—local anesthetic combinations will be preferred for both prolonged continuous spinal or epidural anesthesia and for microsphere-based prolonged peripheral nerve blockade. Both of these embodiments will be useful in the management of cancer pain and chronic pain.

Vanilloids have an antagonist, capsazepine. Injection of capsazepine reverses established block from a vanilloid-site 1 toxin combination. This affords the first method for reversing nerve blockade when it is no longer desired.

Due to the high potency and favorable physical chemistry, combination microspheres with vanilloids, site 1 toxins, and local anesthetics can be constructed to produce ultra-long duration blocks (several weeks to months) for use in cancer and chronic pain. Existing local anesthetics are of very low potency, meaning that for nerve blockade in humans, between 5 and 30 mg/hour may be needed to maintain analgesia. The site 1 toxins are much more potent on a mass basis, meaning that microgram quantities can block nerves. Site 1 toxins, unlike local anesthetics alone, can therefore be used to provide very prolonged block (e.g. weeks to months) from microspheres using small quantities of injected polymer to mini local tissue reactions.

I. FORMULATIONS

Site 1 Sodium Channel Blockers

Site I sodium channel blockers include tetrodotoxin (TTX), saxitoxin (STX), decarbamoyl saxitoxin, neosaxitoxin, and the gonyautoxins (referred to jointly herein as "toxins"). The preferred toxins are TTX and STX.

Tetrodotoxins are obtained from the ovaries and eggs of several species of puffer fish and certain species of California newts. Chemically, it is an amino perhydroquinaoline. See *Pharmacological Reviews*, Vol. 18 No. 2, pp. 997–1049. Tetrodotoxin alone is too toxic to be used as an anesthetic.

Saxitoxin was first extracted from the Alaska butterclam, *Saxidomus gigantcus*, where it is present in algae of the genus Gonyaulax. The reported chemical formula is $C_{10}H_{15}N_7O_3.2HCl$. It is believed the toxin has a perhydropurine nucleus in which are incorporated two guanidinium moieties. Saxitoxin is too toxic to be used alone as a local anesthetic.

During the past few years, a number of unusual polypeptides have been isolated from the paralytic venoms of the fish hunting cone snails of the genus Conus found in the Philippine archipelago. Many of these, designated "conotoxins," have been discovered to affect ion channel function. The paralytic a, m, and w conotoxins block nicotinic acetylcholine receptors, sodium channels, and voltage sensitive calcium channels, respectively (reviewed in Olivera et al., "Diversity of Conus neuropeptides," *Science*, 249:257–263, 1990.). Those which block sodium channels can be used in the same manner as the tetrodotoxins and saxitoxins.

Although the most widely known site 1 toxin, tetrodotoxin, is effective, it will be expensive for clinical use since it must come from the puffer fish; when the endosymbiotic bacteria that makes TTX is grown ex vivo, its production of TTX diminishes. Saxitoxin and its derivatives can be produced in bioreactors from algae. The two derivatives, neosaxitoxin and decarbamoyl saxitoxin, have advantages in terms of the production process and potency. Neosaxitoxin and decarbamoyl saxitoxin are potentially more potent and may have advantages over saxitoxin in formulation. Saxitoxin and these two derivatives all give markedly synergistic block and prolonged block (1–2 days in rat sciatic nerve in vivo) when combined with bupivacaine or epinephrine.

An advantage of using the toxins is that an overdose can be readily counteracted by administration of antibodies to the toxins.

Vanilloids

The vanilloids are a group of compounds that have been studied for producing and relieving pain in other contexts. The most widely studied is capsaicin (the burning component of chili peppers), but other compounds, including resiniferotoxin, are under intensive study. Vanilloid receptors mediate heat pain. Topical capsaicin is used for pain in shingles, arthritis, and other conditions. Capsaicin has previously been used in animal models to injury peripheral nerves for study purposes, and to make animals insensitive to pain. It is selectively toxic to C-fibers, so that it produces greater impairment of pain sense than motor function. Previous work emphasized the nerve-injuring actions of capsaicin. Much lower concentrations of capsaicin (and resiniferotoxin) produce reversible, non-nerve-injuring reversible nerve blockade than conventional local anesthetics. This nerve blockade is selective for pain, not light touch or motor function.

The doses of capsaicin or resiniferotoxin required to produce prolonged block (e.g. 2 days in rats, probably 3–4 days in humans) in combination with TTX are more than 5-fold below the threshold for block from capsaicin or resiniferotoxin alone, and are far below the threshold for producing local nerve injury or systemic toxic effects.

Capsaicin, derived from hot peppers, (trans-8-methyl-N-vanillyl-6-nonenamide), and synthetic capsaicin (N-vanillyl-nonanamide), are well known for use as an analgesic, as described in U.S. Pat. No. 4,313,958 to LaHann. It is described for topical use in an ointment in combination with between 0.5 and 20% local anesthetic such as lidocaine or benzocaine, alone or in combination with a topical steroid such as hydrocortisone or betamethasone, in U.S. Pat. Nos. 5,008,289 and 4,997,853 to Bernstein. Other vanillyloids include beta-aminoethyl-substituted phenyl compounds, such as beta-aminoethoxy-substituted compounds, described by Gardner, et al., in U.S. Pat. No. 5,045,565, methylene substituted-N-phenylmethyl aikanamides, described by Janusz, et al., in U.S. Pat. No. 4,544,668, N-[(substituted phenyl)methyl]-cismonounsaturated alkenamides, preferably N-vanillyl-cis-monounsaturated alkenamides, and pharmaceutically acceptable salts, described in U.S. Pat. No. 4,493,848 to LaHann, et al., beta-aminoethyl-substituted phenyl compounds described in U.S. Pat. No. 5,099,030 to Gardner, and N-[(substituted phenyl)methyl]diunsaturated amides or pharmaceutically acceptable salts, described by LaHann, et al., in U.S. Pat. No. 4,544,669. Other useful compounds are resinifera compounds.

Vanilloids have an antagonist, capsazepine. Injection of capsazepine reverses established block from a vanilloid-site 1 toxin combination. This affords the first method for reversing nerve blockade when it is no longer desired

Local Anesthetics

As used herein, the term "local anesthetic" means a drug which provides local numbness or pain relief. A number of different local anesthetics can be used, including dibucaine, bupivacaine, ropivacaine, etidocaine, tetracaine, procaine, chlorocaine, prilocaine, mepivacaine, lidocaine, xylocaine, and mixtures thereof. The preferred anesthetic is bupivacaine or dibucaine, most preferably in the free base, alternatively in the form of a salt, for example, the hydrochloride, bromide, acetate, citrate, or sulfate. Bupivacaine is a particularly long acting and potent local anesthetic when incorporated into a polymer. Its other advantages include sufficient sensory anesthesia without significant motor blockage, lower toxicity, and wide availability. Local anesthetics that produce modality-specific blockade, as reported by Schneider, et al., *Anesthesiolosy*, 74:270–281 (1991), or that possess physical-chemical attributes that make them more useful for sustained release then for single injection blockade, as reported by Masters, et al., *Soc. Neurosci. Abstr.*, 18:200 (1992), can also be used.

Classes of local anesthetics which can be utilized include the aminoacylanilide compounds such as lidocaine, prilocaine, bupivacaine, mepivacaine and related local anesthetic compounds having various substituents on the ring system or amine nitrogen; the aminoalkyl benzoate compounds, such as procaine, chloroprocaine, propoxycaine, hexylcaine, tetracaine, cyclomethycaine, benoxinate, butacaine, proparacaine, and related local anesthetic compounds; cocaine and related local anesthetic compounds; amino carbonate compounds such as diperodon and related local anesthetic compounds; N-phenylamidine compounds such as phenacaine and related anesthetic compounds; N-aminoalkyl amid compounds such as dibucaine and related local anesthetic compounds; aminoketone compounds such as falicaine, dyclonine and related local anesthetic compounds; and amino ether compounds such as pramoxine, dimethisoquien, and related local anesthetic compounds.

The preferred local anesthetics are amino, amid and amino esters, with the most preferred being bupivacaine, with the levoenantiomer being preferred where vasoconstrictor activity of the local anesthetic is desirable.

Vasoconstrictors

Vasoconstrictors which are useful are those acting locally to restrict blood flow, and thereby retain the injected drugs in the region in which they are administered. This has the effect of substantially decreasing systemic toxicity. Preferred vasoconstrictors are those acting on alpha adrenergic receptors, such as epinephrine and phenylepinephrine. Other drugs and dyes vasoconstrict as a side-effect, such as bupivacaine.

Corticosteroids

Corticosteroids that are useful to prolong in vivo nerve blockade include glucocorticoids such as dexamethasone, cortisone, hydrocortisone, prednisone, and others routinely administered orally or by injection. Other glucocorticoids include beclomethasone, betamethasone, flunisolide, methyl prednisone, para methasone, prednisolone, triamcinolome, alclometasone, amcinonide, clobetasol, fludrocortisone, diflurosone diacetate, fluocinolone acetonide, fluoromethalone, flurandrenolide, halcinonide, medrysone, and mometasone, and pharmaceutically acceptable salts and mixtures thereof.

Lipophilic and Amphiphilic Solvents

Lipophilic and/or amphiphilic solvents can be added to the carrier to prolong nerve blockade or local anesthesia. These materials are well known to those skilled in the art and available from a variety of commercial sources. Examples of solvents include alcohols such as ethanol added in a dosage equivalent to approximately 1% alcohol, polyoxyethylene sorbitan derivatives such as polysorbate-80 or Tween, added in a concentration equivalent to between 1% and 3%.

Carriers

These can be provided in any pharmaceutically acceptable carrier for injection, such as water, saline, dextrose solutions, carboxymethylcellulose, mannitol, and buffered solutions.

Polymeric Formulations

Previous work with local anesthetic microspheres has shown that there is considerable local tissue inflammation and acidosis, and ineffective block unless small amounts of anti-inflammatory steroids are co-injected. Steroids have a variety of potential risks in terms of immune suppression and impaired local wound healing, so that a steroid-free prolonged duration block, either as a liquid or as a microsphere-based formulation, would be useful. Examples demonstrate block of the rat sciatic nerve in vivo for 3 to 7 days using bupivacaine-PLGA microspheres with tiny percent loadings of TTX (less than 2%) without any steroid requirement. In contrast, bupivacaine-PLGA microspheres without any steroid cannot produce block longer than 8–12 hours, and with severe local tissue reactions. The combination of TTX-dexamethasone-bupivacaine in microspheres produces even longer block (5 to 20 days), which will be useful for chronic pain and cancer pain.

Polymenc Compositions and Drug Loading

The anesthetic can be incorporated into the microsphere in a percent loading of 0.1% to 90% by weight, preferably 5% to 75% by weight. It is possible to tailor a system to deliver a specified loading and subsequent maintenance dose by manipulating the percent drug incorporated in the polymer and the shape of the matrix, in addition to the form of local anesthetic (free base versus salt) and the method of production. The amount of drug released per day increases proportionately with the percentage of drug incorporated into the matrix (for example, from 5 to 10 to 20%). In the preferred embodiment, polymer matrices with about 75% drug incorporated are utilized. Drug loading depends on the drug, the method used for making and loading the delivery system, and the polymer.

The local anesthetic is preferably delivered to the patient incorporated into a polymer in the form of microparticles, most preferably microspheres. Other forms of the polymers include microcapsules, microencapsulated microspheres, slabs, beads, and pellets, which in some cases can also be formulated into a paste or suspension.

Polymers

The delivery systems are most preferably formed of a synthetic biodegradable polymer, although other materials may also be used to formulate the delivery systems, including proteins, polysaccharides, and non-biodegradable synthetic polymers. It is most preferable that the polymer degrade in vivo over a period of less than a year, with at least 50% of the polymer degrading within six months or less. Polymers should also preferably degrade by hydrolysis by surface erosion, rather than by bulk erosion, so that release is not only sustained but also linear. Exemplary polymers which meet this criteria include some of the polyanhydrides, poly(hydroxy acids) such as co-polymers of lactic acid and glycolic acid wherein the weight ratio of lactic acid to glycolic acid is no more than 4:1 (i.e., 80% or less lactic acid to 20% or more glycolic acid by weight), and polyorthoesters containing a catalyst or degradation enhancing compound, for example, containing at least 1 % by weight anhydride catalyst such as maleic anhydride. Other polymers include protein polymers such as gelatin and fibrin and polysaccharides such as hyaluronic acid.

The polymers should be biocompatible. Biocompatibility is enhanced by recrystallization of either the monomers forming the polymer and/or the polymer using standard techniques.

Although not as preferred, other local carrier or release systems can also be used, for example, the lecithin inicrodroplets or liposomes of Haynes, et al., *Anesthesiology* 63, 490–499 (1985), or the polymer-phospholipid microparticles of U.S. Pat. No. 5,188,837 to Domb. As used herein, the term "polymer" refers interchangeably with the various carrier forms, including the lipid based carriers, unless otherwise specified.

Methods of Manufacture of Delivery Systems

Methods for manufacture of suitable delivery systems for administration of the local anesthetic in combination with glucocorticoid are known to those skilled in the art. The local anesthetic is incorporated, at least in part, into the delivery system. The glucocorticoid can be incorporated into all or a part of the delivery system(s), and/or administered adjacent to or with the delivery systems as a formulation.

As used herein, polymeric delivery systems include microparticles, slabs, beads, pastes, pellets, and suspensions. Microparticles, microspheres, and microcapsules are collectively referred to herein as "microspheres". Microspheres are used in the most preferred embodiment. The microspheres are preferably manufactured using methods for manufacture of microspheres which are well known and are typified in the following examples, most preferably a method that evenly disperses the anesthetic throughout the delivery system, such as solvent casting, spray drying or hot melt, rather than a method such as compression molding. A desired release profile can be achieved by using a mixture of microspheres formed of polymers having different release rates, for example, polymers releasing in one day, three days, and one week, so that linear release is achieved even when each polymer per se does not release linearly over the same time period. In the preferred embodiment for administration by injection, the microspheres have a diameter of between approximately 10 and 200 microns, more preferably between 20 and 120 microns.

II. APPLICATIONS

The formulations can be used for two to five day intercostal blockade for thoracotomy, or longer term intercostal blockade for thoracic post-therapeutic neuralgia, lumbar sympathetic blockade for reflex sympathetic dystrophy, or three-day ilioinguinal/iliohypogastric blockade for hernia repair. Modality-selective blockade may be useful for epidural infusion for postoperative pain or pain of childbirth, where it is desirable to have pain relief without vasodilation or loss of motor strength. The formulations will typically be administered using standard techniques for administration of local anesthetics or nerve blockade.

Site 1 toxins can be combined with FDA-approved amphiphilic vehicles, including non-ionic detergents or other solvents, such as ethanol, polyoxyethylene sorbitan derivatives such as Tween, in concentrations of Tween ranging from 0.3%–3%, dimethylsulfoxide (DMSO) and others. The site 1 sodium channel blockers, together with the amphiphilic or lipophilic substance, are administered locally at the site where the nerve is to be blocked, preferably as a solution.

Dosage ranges are between 5 and 175 mg for bupivacaine alone, between 28 and 2800 micrograms for tetrodotoxin alone, between 7 and 2800 micrograms tetrodotoxin alone or in combination with bupivacaine in combination with between 1:200,000 and 1:5,000,000 epinephrine, 7 and 700 micrograms saxitoxin alone or in combination with bupivacaine, one to 700 micrograms saxitoxin alone or in combination with bupivacaine with between 1:200,000 and 1:5,000,000 epinephrine, and any of these combinations with between 0.05 and 1 mg dexamethasone/mg.

Applications of Polymeric Formulations

A suspension of microspheres which are administered by injection at the site where pain relief is to be achieved, or in the vicinity of nerves which innervate the site where pain relief is to be achieved. The microspheres may be injected through a trochar, or the pellets or slabs may be surgically placed adjacent to nerves, prior to surgery or following repair or washing of a wound. The microspheres can be administered alone when they include both the glucocorticoid and local anesthetic or in combination with a solution including a steroidal anti-inflammatory or other glucocorticoids in an amount effective to prolong nerve blockade by the anesthetic released from the microspheres. The suspensions, pastes, beads, and microparticles will typically include a pharmaceutically acceptable liquid carrier for administration to a patient, for example, sterile saline, sterile water, phosphate buffered saline, carboxymethylcellulose, mannitol, or other common carriers.

In a preferred embodiment, controlled release of tetrodotoxin from a polymer microsphere is used to provide prolonged nerve blockade. The epinephrine is added to the injection solution to slow initial systemic release of tetrodotoxin, in order to provide an added margin of safety (resulting in minimal toxicity from the TTX). This formulation can be combined with dexamethasone to prolong duration to provide longer nerve blocks than are currently available by other liquid or controlled-release technologies, with durations possibly in the range of 2 to 4 weeks or more.

Potential applications include 2 to 14 day intercostal blockade for thoracotomy, or longer term intercostal blockade for thoracic post-therapeutic neuralgia, lumbar sympathetic blockade for reflex sympathetic dystrophy, or 2 to 6 week block of peripheral nerves, celiac plexus, or autonomic ganglia for patients with cancer.

III. EXAMPLES

The present invention will be further understood by reference to the following non-limiting examples. Abbreviations used include: TTX, tetrodotoxin; BPV, bupivacaine;

Epi, epinephrine; DEB, duration of effective block; $ED_{50}$, effective dose 50%; $EC_{50}$, effective concentration 50%; $LD_{50}$ lethal dose 50%; TPR, tactile placing response; EPT, extensor postural thrust; MOPS, morpholinopropanesulfonic acid; TN, thermal nociception; PPR, positional placing response, Hop, hopping; EPT, extensor postural thrust.

Materials and Methods

Animal Care

Animals were cared for in compliance with protocols approved by the Children's Hospital Animal Care and Use Committee. Sprague-Dawley rats were obtained from Charles River Laboratories (Wilmington, Mass.). They were housed in groups and kept in a 6 am–6 pm light-dark cycle. Young adult male Sprague-Dawley rats weighing 310–420 g were used. Rats were handled repeatedly by the investigators to diminish effects due to stress induced analgesia. Rats that became flaccid as a result of TTX injection were anesthetized with halothane (with bag and mask ventilation) then euthanized with carbon dioxide.

Sciatic Blockade Technique

Prior to nerve block injections, rats were anesthetized briefly with halothane (2 to 4% inspired concentration in 100% oxygen) by facemask. This reduces aversive behaviours with repeated procedures and makes injection more precise. A brief halothane anesthetic has no effect on measures of blockade after the rats emerged from anesthesia, and block durations are also unaffected. The duration of anesthesia was usually less than 2 minutes. Halothane was withheld from one control group described below.

The block was initiated by introducing a 23G needle postero-medial to the greater trochanter, pointing in an anteromedial direction. Once bone was contacted, the needle was withdrawn 1 mm and drug was injected. The final volume of injectate was 0.3 ml of test solution except in one set of experiments, where it was 0.1 ml. The left leg was always used for blocks; the right served as control.

In most cases, injected doses are reported by concentration (molarity). Since the volume of injectate is 0.3 ml (except where stated otherwise), 10 $\mu$M TTX corresponds to approximately 1 $\mu$g of TTX (actually 0.96 $\mu$g), 20 $\mu$M corresponds to 2 $\mu$g, etc. 15.4 mM bupivacaine corresponds to 0.5% bupivacaine, 7.7 mM to 0.25% etc. 55 $\mu$M Epinephrine corresponds to 1:100,000 epinephrine. For the determination of the $LD_{50}$, the dose in nmoles•$kg^{-1}$ was considered a more relevant unit.

Subcutaneous Injection Technique

The nuchal area was shaved, then the skin was lifted away from underlying structures. A 23 G needle was inserted subcutaneously, then advanced anteriorly parallel to the axis of the body to a distance of approximately 1 cm (in order to avoid back leakage of drug through the skin puncture site). The volume injected varied depending on the dose delivered, the concentration of the solution used and the weight of the rat; volumes were 0.25 to 0.3 ml per 300 g weight.

Neurobehavioural Assessment of Nerve Blockade

The effectiveness of block was measured at various time points, applying modifications of the methods of Thalhammer et al., *Anesthesiology* 82, 1013–1025 (1995), as detailed below. In all experiments, the person testing the rats was blinded to what drug was injected into any given rat.

The following modalities/functions were measured:

Blockade of thermal nociception (TN) was assessed by a modified hotplate test, Masters, et al., *Anesthesiology* 79, 001–007 (1993). Hind paws were exposed in sequence (left then right) to a hot plate at 56° C. (Model 39D Hot Plate Analgesia Meter, IITC Inc., Woodland Hills, Calif.), and the time (thermal latency) that the animal left its paw there was measured with a stopwatch. After 12 seconds, the paw was removed by the experimenter to avoid injury to the animal or the development of hyperalgesia. This test was repeated three times (with a ten-second pause between tests) for each rat at every time-point. It is important to emphasize that while sensation of the lateral foot is mediated by the sciatic nerve, the hip and knee flexion necessary to remove the foot from the hot plate is mediated by the femoral nerve, which was not blocked. Therefore this test was quite specific for nociceptive block.

Positional placing response (PPR) tests proprioception primarily. Under ordinary circumstances, a prone rat will respond to having a hindpaw pulled back (with the dorsum in contact with the table surface) by returning it to a position alongside its flank, with the claws splayed (score=1). Blockade results in the limb trailing behind the rat with the claws clubbed (score=4). If the foot is returned fully to the flank but the digits are clubbed, the score is 2. Any other outcome (e.g., foot out at an angle) is a 3.

Hopping is a complex integrative test of proprioceptive and motor function. When suspended above a horizontal surface in the hands of an experimenter so that only one foot touches that surface, a rat will hop when its body is slowly moved laterally. It will not do so if there is sensory or motor block. This was scored (1 or 0) according to whether the animal could hop or not.

Extensor Postural Thrust (EPT). The rat was held with its posterior placed at a digital balance on which it could bear weight with one hindpaw at a time. The maximum weight that the rat could bear without its ankle touching the balance was measured.

Data Processing

The effects of the various drug combinations are primarily reported in terms of duration of effective block (DEB). The DEB for thermal nociception (DEB-TN) is the time required for thermal latency to return to a value of 7 seconds (which is 50% of maximal block when a baseline thermal latency of approximately 2 seconds is taken into account). The DEB for PPR (DEB-PPR) is the time that it took for function to return to a score of 2 (4 being a complete block). The DEB for hopping (DEB-Hop) was defined as the midpoint between the last recorded timepoint at which the animal was unable to hop and the first timepoint where this ability had returned. The DEB for EPT (DEB-EPT) data was defined as the time for weight bearing to return halfway to normal from maximal block. The halfway point for each rat was determined by the following calculation: Midpoint=((Highest weight borne by either leg)–(lowest weight borne by blocked leg))÷2. This method of analysis measures the dynamic component of the weight/force exerted by the rat, as it subtracts the weight of the flaccidly paralyzed foot from the total force exerted.

Animals that did not survive the acute block were not included in the calculation of DEB. However, is important to emphasize that the DEBs of all other animals were included in the calculations of average DEBs. The DEB for the appropriate modality was considered 0 (zero) for all "unsuccessful" blocks, defined as injections which did not result in a thermal latency of at least 7 seconds, a PPR score of 2 or higher, a hopping score of 0, or an EPT suppression of at least 50%. Thus "missed" blocks are not excluded from analysis. Pilot studies show that injection of bupivacaine 0.5%, 0.3 ml results in a "missed block" rate by these investigators of 0% (n=18). Therefore, causes of failure to achieve block with some solutions used herein are probably not due to needle placement but reflect pharmacologically significant factors such as drug potency, concentration, volume, spread through tissues, partitioning between aqueous and lipophilic compartments, etc.

Statistical Analysis

Values are usually reported as means with standard deviations. Unless stated otherwise, statistical inferences (p-values) are made with Student's t-test (paired in comparisons between injected and contralateral legs, unpaired in all other cases), or with ANOVA. A subset of the data might have non-normal distributions due to the inclusion of zero-duration blocks, as described in the preceding paragraph.

In most circumstances, a p-value of 0.05 indicates statistical significance. When numerous comparisons are made, the Bonferroni correction factor was used to determine the p-value. Thus, the "significant" p-value is 0.05 divided by the number of comparisons. For example, if three comparisons are made, the p-value required would be 0.05 divided by three, or 0.017.

Logit (logistic regression) analyses were used to derive and compare $LD_{50}$ and $EC_{50}$. These data analyses were conducted using Stata statistical software (Stata Corporation, College Station, Tex.).

Examples 1–3 demonstrate that tetrodotoxin without epinephrine produces sciatic nerve blockade, but with considerable toxicity at most effective doses. Epinephrine reduces the $EC_{50}$ of tetrodotoxin for nociception from 37.6 $\mu$M to 11.5 $\mu$M, and prolongs its duration, such that reversible blocks lasting over 13 hours were achieved. Epinephrine reduces measures of systemic distribution and increases the $LD_{50}$ of TTX from 40 nmoles•kg$^{-1}$ to 53.6 nmoles•kg$^{-1}$, thus more than quadrupling the therapeutic index. Bupivacaine increases the local anesthetic potency of tetrodotoxin, reduces its systemic toxicity and, when co-injected subcutaneously, increases the $LD_{50}$ from 43.7 nmoles•kg$^{-1}$. Addition of epinephrine does not further improve the effectiveness of the bupivacainetetrodotoxin combination.

Example 1

Local Anesthetic Properties and Toxicity of TTX

Stock TTX Solutions

Tetrodotoxin stock solutions were made by dissolving 1 mg TTX (Sigma Chemical Co., St. Louis, Mo.) in 10 ml of 20 mM citrate buffer (Na citrate:citrate, 55:45), pH 4.45. Bupivacaine hydrochloride (Sigma Chemical Co., St. Louis, Mo.) was formulated in 10 mM morpholinopropane-sulfonic acid (MOPS, Sigma Chemical Co., St. Louis, Mo.) titrated to a pH of 6.55 with NaOH. This stock solution was most commonly diluted with TTX stock and saline (Baxter Healthcare Corp., Deerfield, Ill.) toward a target concentration of 15.4 mM (≈0.5%). Epinephrine from a commercial 1:1000 (1 $\mu$g•$\mu$l$^{-1}$) solution (American Regent Laboratories, Inc., Shirley, N.Y.) was diluted to the desired concentration. A fresh vial of epinephrine was used every day.

Local Anesthetic Properties and Systemic Toxicity of TTX

Figure 1:
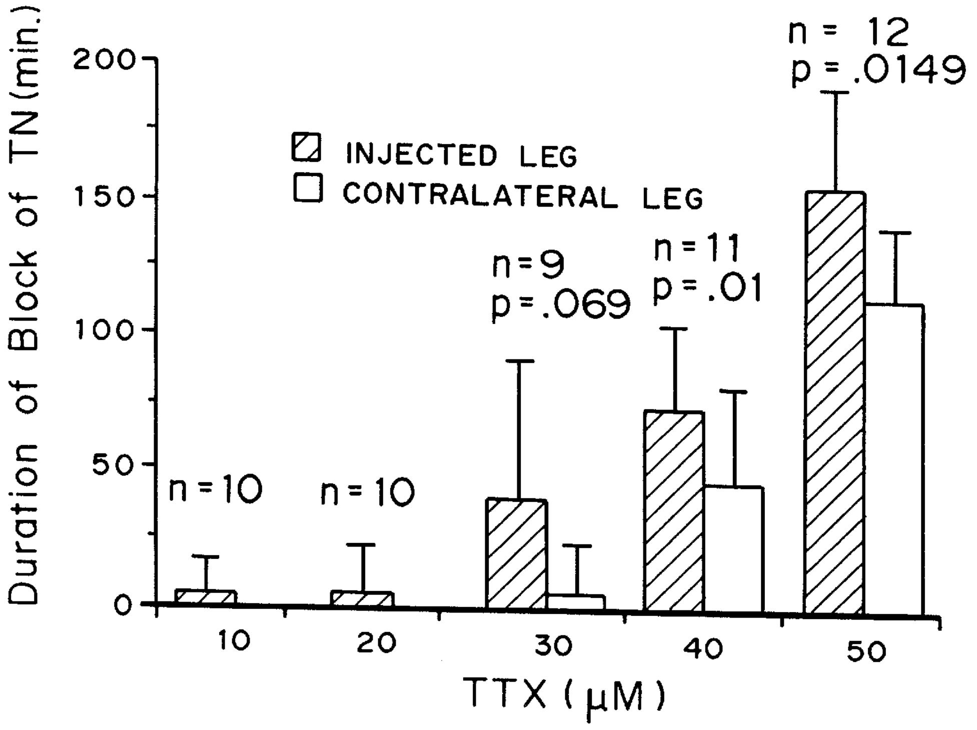
FIG. 1 is a graph comparing the durations of block of thermal nociception (DEB-TN) in the injected (dark bars) and contralateral (white bars) legs at various concentration of TTX (10, 20, 30, 40 and 50 micrograms). Mean±SD. The p values comparing DEB-TN in both legs were calculated with a paired t-test. Injection of high concentrations was associated with pronounced blockade of the contralateral leg.

Groups of rats received sciatic nerve injections with 10, 20, 30, 40 and 50 $\mu$M TTX, in 0.3 ml of saline (corresponding to 1 to 5 $\mu$g, respectively). The duration of nociceptive blockade increased with increasing concentration beyond 20 $\mu$M TTX (FIG. 1 and Table 1). As a control, six rats were injected with 0.3 ml 0.9% saline. None of them developed any deficits of the modalities measured.

TABLE 1

Duration of thermal noiceptive block (DEB-TN) from TTX alone or with 55 $\mu$M Epinephrine

| Concentration TTX ($\mu$M) | DEB-TN (min.) TTX Alone | n | With Epinephrine | n | p-value |
|---|---|---|---|---|---|
| 10 | 4 ± 17 | 10 | 266 ± 250 | 10 | .009 |
| 20 | 5 ± 16.6 | 10 | 446 ± 283 | 10 | .0003 |
| 30 | 39 ± 50 | 9 | 656 ± 123 | 10 | $5.2 \times 10^{-9}$ |
| 40 | 72 ± 30 | 11 | 655 ± 186 | 10 | $4.2 \times 10^{-6}$ |
| 50 | 154 ± 36 | 12 | 795 ± 230 | 11 | $3.6 \times 10^{-6}$ |
| 100 | — | 6/6 dead | 979 ± 218 | 2 (4/6 dead) | — |

Value for DEB-TN are mean±SD. p-values comparing DEB-TN of TTX with and without epinephrine were determined by Student's t-test.

The standard deviations of the DEBs were large relative to the mean values, especially at the lower concentrations. The coefficients of variation for DEB with 10, 20, 30, 40 and 50 $\mu$M of TTX are 425%, 332%, 128%, 41%, and 23%. For comparison, the coefficient of variation for block with 15.4 mM (0.5%) bupivacaine, which gives a DEB-TN approximately equal to that of 50 $\mu$M TTX, was 26%. The large coefficients of variation for TTX resulted from the fact that in calculating the mean DEB, unsuccessful blocks (as defined in Methods) were included, with a defined DEB of zero. All failed blocks were included in the calculations because (a) there was no a pinoni way to distinguish between blocks that failed because a given drug was too weak and a misplaced injection, and (b) the rate of successful block with 15.4 mM bupivacaine was 100%, suggesting that the drug was being deposited at an effective location. As discussed below, unsuccessful blocks were very common at the lower concentrations of TTX. When the zero DEBs are assumed to be missed blocks and are discarded, the standard deviations become much smaller. For example, the coefficient of variation for the DEB-TN of 30 $\mu$M TTX drops from 128% to 38%, for 40 $\mu$M TTX drops from 41% to 24%.

At low concentrations of TTX, successful TN block was infrequent but was always unilateral in the injected leg. As the dosage of TTX was increased, the number of successful TN blocks increased, but the fraction of successful blocks that were associated with sensory and motor deficits in the contralateral (non-injected) limbs also rose markedly (Table 2). At high concentrations, TN blockade was uniformly "successful", but the contralateral leg was also strongly affected, presumably by sublethal systemically distributed toxin (FIG. 1). The deficits were significantly greater in the injected than in the non-injected limbs. None of the rats showed deficits in the contralateral leg only. These observations imply that deficits in behaviour from TTX alone resulted from a combination of local blockade and systemic effects.

TABLE 2

Frequency of Successful Thermal Nociceptive Blocks in the Injected and Contralateral Leg

| TTX ($\mu$M) | % Successful blocks Injected leg | % Successful Blocks with Contralateral Block |
|---|---|---|
| 10 | 10% (1/10) | 0% (0/1) |
| 20 | 10% (1/10) | 0% (0/1) |

TABLE 2-continued

| Frequency of Successful Thermal Nociceptive Blocks in the Injected and Contralateral Leg | | |
|---|---|---|
| TTX ($\mu$M) | % Successful blocks Injected leg | % Successful Blocks with Contralateral Block |
| 30 | 44% (4/9) | 25% (1/4) |
| 40 | 91% (10/11) | 80% (8/10) |
| 500 | 100% (12/12) | 100% (12/12) |

For each concentration of TTX in the first column, the second column shows the percentage of injections that resulted in a successful block (defined as resulting in a thermal latency of at least 7 seconds). The third column shows the percentage of those successful blocks that were associated with blockage in the contralateral limb.

Control experiments reconfirmed that the contralateral deficits were unrelated to the presence or absence of a brief halothane general anesthetic; impairment was similar in animals having an injection when awake (n=4) or anesthetized (data not shown). Furthermore, animals given halothane without sciatic nerve block (n=3) had normal latencies in the contralateral leg upon awakening.

Another indication that the observed deficits in both the injected and contralateral legs were at least partly due to systemic toxin was the finding that subcutaneous injection of 40 $\mu$M TTX at the nuchal midline was able to produce increased thermal latency in both legs. Thermal nociception in the left leg was affected, with a DEB-TN of 100±32 min., comparable to the 72±30 min. for the same concentration of TTX injected at that leg's sciatic nerve.

Deficits in the contralateral leg were accompanied by a range of symptomatology varying from none to death, depending on the TTX concentration. Some rats developed lower extremity impairment of TN without appearing grossly sick nor weak (although fine testing, such as EPT would reveal marked weakness, see below). There was overt toxicity at the higher concentrations. One of 12 animals in the 40 $\mu$M group and 3 of 15 in the 50 $\mu$M group died, and many others appeared lethargic or flaccid, or had difficulty breathing. All of six animals given 100 $\mu$M TTX injections (=20 $\mu g \cdot kg^{-1}$ or 62 $nmole \cdot kg^{-1}$) died within half an hour. The $LD_{50}$ from percutaneous injection of TTX alone was 40 $nmole \cdot kg^{-1}$ (12.9 $\mu g \cdot kg^{-1}$; 95% confidence intervals 34.8 $nmole \cdot kg^{-1}$ to 45.2 $nmole \cdot kg^{-1}$).

Pattern of Functional Impairment from TTX

Figure 2:
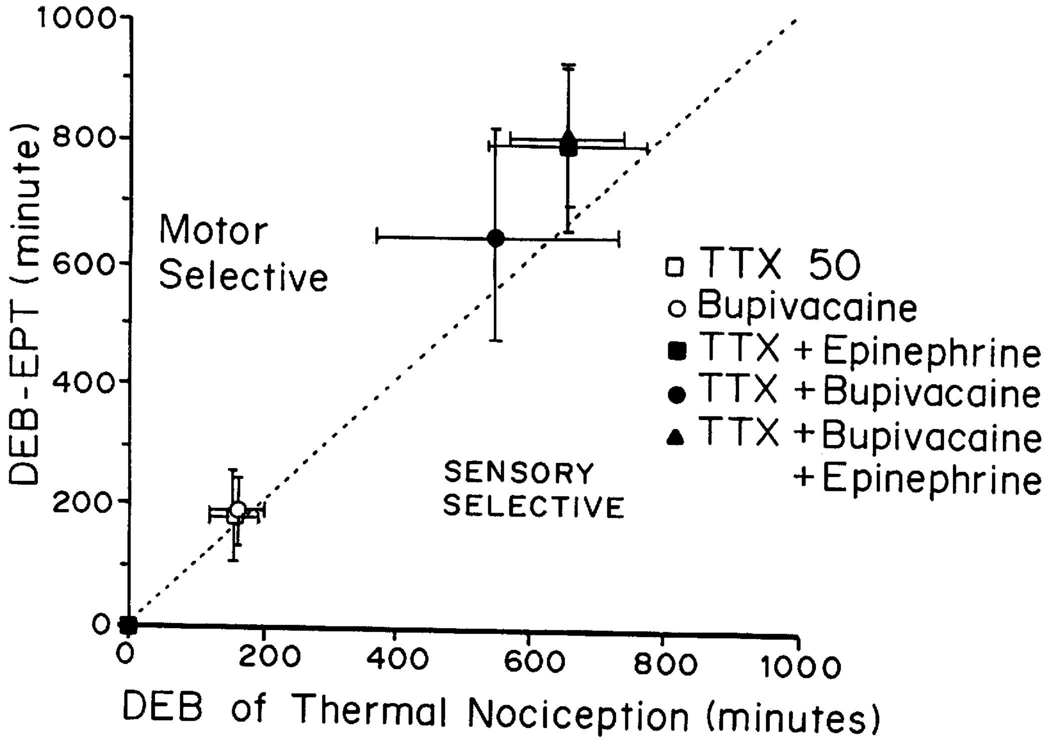
FIG. 2 is a graph comparing the duration of block (DEB) for thermal nociception (sensory function) and EPT (extensor postural thrust, motor function) for TTX 50 $\mu$M (5

Block durations following TTX injection for thermal nociception and extensor postural thrust (a measure of motor block) were approximately equal (FIG. 2). At low concentrations (e.g. 30 $\mu$M, Table 3) there was no statistically significant difference between any of the modalities. However, at higher doses, DEB-Hop was shorter than the others. For example, 50 $\mu$M TTX resulted in the following DEBs: EPT 179±73 min., TN 154±36 min., PPR 118±92 min., Hop 78±107 min. (The p-value of the ANOVA for all four modalities was 0.02. For the t-test comparing DEB-EPT and DEB-Hop, p=0.013. As there were three comparisons to EPT, the significant pvalue is 0.017). The shorter DEB for hopping was due to the fact that 6 out of 12 (50%) rats injected with 50 $\mu$M TTX had unimpaired hopping while both TN and EPT were maximally affected. Three out of 12 (25%) rats also had unimpaired hopping while both TN and EPT were maximally affected. Three out of 12 (25%) rats also had unimpaired PPR (DEB-PPR also was shorter than DEB-EPT, but the difference was not statistically significant).

TABLE 3

| Duration of effective block for each of the functional modalities. | | | | | | |
|---|---|---|---|---|---|---|
| | Duration of Effective Block (in minutes.) | | | | | |
| Drug | TN | PPR | Hop | EPT | n | ANOVA |
| TTX alone | 39 ± 50 | 25 ± 52 | 27 ± 67 | 55 ± 54 | 9 | 0.65 |
| Bupivacaine alone | 161 ± 42 | 162 ± 44 | 143 ± 48 | 190 ± 56 | 18 | 0.04 |
| TTX + Epinephrine | 656 ± 123 | 846 ± 126 | 787 ± 137 | 860 ± 109 | 11 | 0.0003 |
| TTX + Bupivacaine | 550 ± 181 | 629 ± 182 | 587 ± 190 | 642 ± 174 | 10 | 0.63 |
| TTX + Bupivacaine + Epinephrine | 659 ± 83 | 766 ± 98 | 731 ± 125 | 804 ± 115 | 10 | 0.03 |

In this table, TTX=30 $\mu$m (3 $\mu$g), Epinepe=55 $\mu$M (1:100,000), Bupivacaine=15.4 mM (0.5%). Values are mean±SD. TN=thermal nociception, PPR=positional placing response (proprioception), Hop=hopping, EPT=extensor postural thrust (motor function). ANOVA lists the p-value of the comparison of the four modalities for each drug.

This lack of impairment of hopping (and to a lesser extent, PPR) was not seen with 15.4 mM (0.5%) bupivacaine, where all four modalities were impaired in all rats (Table 3). However, it occurred in 10 100% of rats injected with 40 $\mu$M TTX subcutaneously in the neck (n=12).

Example 2

TTX and Bupivacaine and/or Epinephrine

Effect of Second Drug on Duration and Effectiveness

1) Epinephrine

Groups of rats were injected with 10 to 50 $\mu$M TTX made up in 55 $\mu$M (1:100,000) epinephrine. The vasoconstrictor greatly increased the duration of blockade of all concentrations of TTX (FIG. 3, Table 1). Concentrations of TTX that had little effect alone produced strong anesthesia when co-injected with epinephrine, while the higher concentrations had their DEBs prolonged several-fold. The effect of the addition of epinephrine on the frequency with which TTX achieved maximal thermal nociceptive block (i.e. thermal latency=12 seconds) was also measured, as shown in FIG. 4. Groups of rats were given sciatic nerve blocks with various concentrations of TTX with or without epinephrine. The fraction developing a maximal block was plotted against the concentration delivered, and the $EC_{50}$ (the concentration required to achieve maximal block—i.e. thermal latency of 12 seconds—in 50% of rats) was derived for each group. The $EC_{50}$ was decreased by more than threefold by addition of epinephrine, from 37.6 $\mu$M (95% confidence interval 34.2 to 41 $\mu$M) to 11.5 $\mu$M (95% confidence interval 8 to 15 $\mu$M) ($p<0.0001$).

The increase in DEB-TN due to epinephrine was concentration-dependent (FIG. 5). Very low concentrations of epinephrine were still capable of yielding very prolonged blockade. For example, 30 $\mu$M TTX with 1.1 $\mu$M epinephrine (1:5,000,000, one twenty-fifth of the concentration traditionally used with local anesthetics) had no signs of systemic toxicity and had a DEB-TN of 408±243 min, a ten-fold prolongation over the DEB-TN of 30 $\mu$M TTX alone (39±50 mins.) (p=0.002). Although the DEB-TN for 30 $\mu$M TTX with 0.6 $\mu$M epinephrine (131±132 minutes) was considerably increased over that of TTX alone, the difference was not statistically significant (p=0.06).

The potential for even longer blockade was demonstrated by delivering the same dose of TTX (in $\mu$g) in a 0.1 ml volume (i.e. three times the concentration). When rats were injected with 3 $\mu$g of TTX with epinephrine in 0.1 ml (90 $\mu$M), the resulting DEB-TN was 948±100 min. (n=6), a 45% increase in block duration over 3 $\mu$g in the more dilute formulation (p=0.00023), with no overt toxicity.

2) Bupivacaine

When the sciatic nerve was blocked with various combinations of TTX and bupivacaine (n=4 to 24), a marked prolongation of DEB was observed. For example, the DEB-TN for 30 $\mu$M TTX was 39±50 minutes (n=9), that for 15.4 (0.5%) mM bupivacaine was 161±42 minutes (n=18), and the DEB-TN of the combination was 556±147 minutes (n=11, p=$1.15\times10^{-6}$ vs. TTX alone, p=$2.2\times10^{-5}$vs. bupivacaine alone). This result demonstrated that the combination of the two drugs yielded a duration of block greater than the sum of the durations from the individual drugs.

FIG. 6 shows a threedimensional surface that describes the DEB-TN as a function of TTX co-injected with bupivacaine. The endpoints of the curve superimposed on that surface are concentrations of bupivacaine and TTX that separately yield equivalent DEB-TNs (154±36 min. for 50 $\mu$M TTX, 161±42 min. for 15.4 mM bupivacaine). The three points along that line represent the DEB-TN obtained from combinations of lower concentrations of bupivacaine and TTX which should last as long as either drug alone if the combinations were merely additive (i.e. should also last=160 minutes). The ANOVA for the DEB-TN at those three points and for 50 $\mu$M TTX and 15.4 mM bupivacaine yielded p=0.00067.

The dotted lines in FIG. 6 demarcate the point representing the combination of one half the concentration of bupivacaine and one half the concentration of TTX which each provide a DEB-TN of approximately 160 minutes, i.e. 25 $\mu$M TTX with 7.7 mM bupivacaine. The actual DEB-TN from this combination was 276±149 min. (n=24), which was a statistically significant increase over 15.4 mM bupivacaine (p=0.0001) and 50 $\mu$M TTX (p=0.0007). (Since there are six comparisons, the significant p-value=0.0083.) p=values for the other two points along the line were similarly highly significant in comparison to either drug alone (37.5 $\mu$M TTX with 3.85 mM bupivacaine (DEB-TN=317±86 min., n=16)) and 12.5 $\mu$g TTX with 11.6 mM bupivacaine (DEB-TN=294±180 min., n=16)).

The potentiation by TTX of block durations from bupivacaine was dependent on the concentration of TTX, with progressively increasing potentiation as the concentration of TTX was increased. The synergistic effects of the two drugs reached a plateau at around 11.6 mM bupivacaine (for constant dosing of TTX) and 30 $\mu$M TTX (for constant dosing of bupivacaine). The highest DEB-TN, achieved by 50 $\mu$M TTX with 15.4 mM (0.5%) bupivacaine was 559±66 min.

3) Both Epinepihrine and Bupivacaine

Ten rats were injected with 30 $\mu$M TTX with both 15.4 mM bupivacaine and 55 $\mu$M epinephrine. The resulting DEB-TN was 659±83.3 min. This was not a statistically significant improvement over the synergism between 30 $\mu$M TTX and 15.4 mM bupivacaine (550±81 min.), or TTX and 55 $\mu$M Epi (656±123 min.).

Effect of Second Drug on Toxicity

1) Epinephrine

The effects of a vasoconstrictor in the injectate on the systemic actions and lethality of TTX was deterinined. Animals that received 50 $\mu$M TTX (11 to 14 $\mu g\bullet kg^{-1}$) in 55 $\mu$M epinephrine did not appear to be in distress, none died, and the DEB-TN of the contralateral foot was dramatically reduced from 112±27 min. to 2.27±7.5 min. (Table 4).

TABLE 4

Effect of Epinephrine and Bupivacaine on the duration of thermal noiceptive block (DEB-TN) int he contralateral leg.

| TTX | Combined With | DEB-TN | n | p-value |
|---|---|---|---|---|
| 40 $\mu$M | — | 45 ± 34 | 11 | |
| | Epinephrine | 0 | 10 | .003 |
| | Bupivacaine (15.4 mM) | 6.4 ± 23 | 13 | .005 |
| | Bupivacaine (11.6 mM) | 0 | 4 | .003 |
| | Bupivacaine (1.93 mM) | 0 | 4 | .003 |
| 50 $\mu$M | — | 112 ± 27 | 12 | |
| | Epinephrine | 2.26 ± 7.5 | 11 | $5.6\times10^{-9}$ |
| | Bupivacaine (15.4 mM) | 0 | 10 | $2\times10^{-8}$ |

Value of DEB-TN are mean±SD. 'Epinephrine' signifies that the solution contained 55 $\mu$M (1:100,000) Epinephrine. Bupivacaine 15.4 mM=0.5%, 11.6 mM=0.375%, 1.93 mM=0.0625%. p-values (determines by Student's t-test) compare the contralateral DEB-TN of TTX to the contralateral DEB-TN of the same does of TTX in combination with a second drug.

The small degree of contralateral thermal latency in that group was due to one of eleven rats having a contralateral DEB-TN lasting 25 minutes. This reduction in toxicity was documented over a range of dosages. The $LD_{50}$ of TTX was increased from 40 $nmole\bullet kg^{-1}$ (12.9 $\mu g\bullet kg^{-1}$) to 53.6 $nmole\bullet kg^{-1}$ (17.3 $\mu g\bullet kg^{-1}$;95% confidence interval 48.8 to 58.3 $nmole\bullet kg^{-1}$) by the addition of epinephrine (p<0.0001).

2) Bupivacaine

The addition of bupivacaine to the injectate markedly reduced the degree of contralateral block from TTX (Table 4). This effect was seen even at low concentrations of bupivacaine. Furthermore, there were no deaths in rats who received 50 $\mu$M TTX with 15.4 mM bupivacaine (vs. 20% mortality for TTX 50 $\mu$M alone).

In order to elucidate the protective interaction between TTX and bupivacaine, a series of experiments where TTX was injected subcutaneously with or without bupivacaine were performed. The sciatic nerve was used as the site of injection in order to clarify whether impairments measured in the hindpaws were due to systemic toxicity versus some region-specific effect (such as epidural spread of local anesthetics along the sciatic nerve to the epidural space). It was also desirable to eliminate the sciatic nerve and its associated vasculature from the experiments so that any protective effect of bupivacaine would be ascribable to an effect on the surrounding tissue rather than an interaction with a large nerve or blood vessel. The skin at the nuchal midline was selected for this purpose since it is remote from the hindquarters, and it is easy to inject reproducibly in the subcutaneous plane.

Rats were injected subcutaneously with 35 $nmoles\bullet kg^{-1}$ (11.4 $\mu g\bullet kg^{-1}$) of TTX, a dose that would be expected to cause lower extremity deficits based on the results of the experiments described above (0.3 ml of 40 $\mu$M TTX in a 350 g rat is 35 $nmoles\bullet kg^{-1}$). The open squares in FIG. 7 show the time-course of thermal latency in those rats (n=6). A second group was injected with the same dose of TTX made up in 15.4 mM bupivacaine, shown by the filled circles in FIG. 7 (n=6). The peak thermal latency attained by the rats who received TTX with bupivacaine (4.83±0.97 sec.) was considerably less than that achieved by TTX alone (10.8±1.32 sec.) ($p=1.2\times10^5$). Peak thermal latency occurred in an average of 44±24 minutes in the group that received TTX alone, compared to 75±0 min. for the group that received TTX with bupivacaine (p=0.025). These properties are similar to the effect that 55 μM epinephrine has when coinjected with TTX (FIG. 7, filled squares).

The effect of bupivacaine on the lethality of TTX was determined by injecting rats with a range of doses (24.3 to 52.7 nmoles•$kg^{-1}$, or 8 to 17 μg•$kg^{-1}$) of TTX alone (n=101) or TTX with 15.4 mM bupivacaine (n=68). The co-injection of bupivacaine increased the $LD_{50}$ of TTX from 43.7 nmoles•$kg^{-1}$ (14.1 μg•$kg^{-1}$; 95% confidence intervals 42.1 to 45.4 nmoles•$kg^{-1}$) to 47.7 nmoles•$kg^{-1}$ (15.4 μg•$kg^{-1}$); 95% confidence intervals 45 to 50.4 nmoles•$kg^{-1}$) (p<0.007). In those rats that did die from TTX toxicity, the time to death was delayed from 63.5±19 mins. (n=25) to 83±12 min. (n=14) by the addition of bupivacaine (p=0.0003). Thus, the addition of bupivacaine to TTX decreased the magnitude of the thermal latency increase from TTX, reduced the associated mortality, and delayed both latency increases and death.

If this protective effect were mediated at some site remote to the injection site (for example, some unforeseen effect on the nervous system or diaphragm), one would expect the degree of toxicity to be independent of whether the two drugs are injected together. Conversely, if the protective effect were mediated locally, one would expect that it would be necessary for the two drugs to be administered at the same site. To investigate this, TTX was injected simultaneously injected in the nuchal area, and an equal volume of bupivacaine was simultaneously injected in the lower back, at a distance of at least 5 cm. from the site of TTX injection. As shown by the open circles in FIG. 7, there was no reduction (p=0.22) in the peak thermal latency (11.7±0.82 sec.) in the lower extremities when 35 nmoles•$kg^{-1}$ of TTX and 0.3 ml of 15.4 mM bupivacaine were injected at separate sites (n=6), nor was there any delay in the time to peak thermal latency (p=0.87).

Effect of Second Drug on Impairment of Different Functions

The discrepancies between the maximal level of impairment of different functions which had been seen with TTX alone were no longer seen when epinephrine, bupivacaine or both were added. There were, however, small differences between the duration of block of the various modalities (Table 3, FIG. 2). For TTX with epinephrine and TTX with both bupivacaine and epinephrine, DEB-TN was shorter tand the other DEBs. (The ANOVAs comparing the modalities for each drug combination yielded p=0.0003 and 0.03 respectively. For the t-tests comparing DEB-TN to DEB-EPT, p=0.003 and 0.0005 respectively). For TTX with bupivacaine, there were no differences between the DEBs of the modalities (ANOVA p=0.63). (Since there are three comparisons for each drug combination, the significant p-value=0.017.)

Example 3

Effect of STX and Bupivacaine Alone and Following Addition of Dexamethasone 4 μg of STX were combined with 1:100,000 epinephrine and then administered in a sciatic nerve block either with or without 0.5 mg/kg of dexamethasone.

The results are shown in FIG. 8. The duration of effective block of STX+Epi was 20.5±2.8 hours (n=12). The duration of block from STX+Epi+Dexamethasone was 31.3±8.3 hours (n=12). The p-value of the comparison with the STX+Epi group was 0.0009 [unpaired t test].

Example 4

Prolongation of Nerve Blockade by Coadministration of Local Anesthestic with Lipophilic or Amphiphilic Solvents Sciatic nerve blocks with 4 μg of TTX in 0.3 ml of injectate were administered to rats weighing approximately 300 g. The duration of effective block (DEB) was 78 minutes (n=11). A second group of rats was given the same dose of TTX in 1% Tween-20, 1% ethanol in normal salien (n=8). The resulting DEB was over 8 hours. The carrier alone (1% Tween-20, 1% ethanol in normal saline) did not produce any behaviorally detectable nerve block.

Sciatic nerve blocks with 3 μg of TTX in 0.1 ml of injectate were administered to rats weighing approximately 300 g. The duration of effective block (DEB) was 75 minutes (n=5). A second group of rats was given the same dose of TTX in 3% Tween-80 in normal saline. The resulting DEB was 197 mins (n=5). The carrier alone (3% Tween-80 in normal saline) did not produce any behaviorally detectable nerve block.

Example 5

Tetrodotoxin with Bupivacaine and Epinephrine with 0.2% Dexamethasone

In the correct proportions, Tetrodotoxin (TTX) with Epinephrine, when given as a liquid preparation, provides a nerve block that lasts over half a day in a rat, which is longer than what is currently available. This can be extrapolated to an even longer blockade with less toxicity when this preparation is used in larger animals, for example, humans. Toxicity is minimal. The combination of tetrodotoxin with bupivacaine also provides blockade with durations of about 10 hours. Its advantages are similar to those of tetrodoxin with epinephrine. The durations can be even more prolonged when saxitoxin (STX) is used in lieu of TTX (blockade from STX+epinephrine and STX+bupivacaine both last about 20 hours). Combination of site I sodium channel blockers with vasoconstrictors and/or bupivacaine and dexamethasone (a corticosteroid) can produce blockade in excess of 30 hours.

Tetrodotoxin with Bupivacaine and Epinephrine provides a nerve block that is approximately two hours longer than that of tetrodoxin with epinephrine, with similar advantages. These formulations can provide a nerve block lasting two to six days, approximately 50 to 100 times more potent than conventional local anesthetics. Addition of 0.2% dexamethasone extends the block to eight to thirteen days.

Example 6

Administration of Toxin with Capsaicin for Modality-Selective Local Anesthesia Blockade of thermal nociception is assessed by measuring the time (latency) that a rat will rest his foot on a 56° C. hot plate. If the rat does not remove his foot in 12 seconds, it is removed by the examiner to prevent skin burns. Baseline latency is 2 seconds. Adjusted latency is the measured latency minus this baseline, i.e. a maximum of 10 seconds, and a minimum of 0. Duration of block is defmed as the time required for the adjusted latency to return to 5 seconds.

A group of rats (n=9) were injected with 4 μg of TTX ("T4" in FIG. 9). The block lasted 78±32 minutes. Another group of rats were injected with bupivacaine 0.125%, with a duration of block of 104±18 minutes. Two further groups of rats (n=4 each), were injected with 4 μg of TTX in combination with 30 μg of capsaicin (Cap+T: Noci I and II). The duration of block was increased to 7 to 8 hours. The block in these cases was of the conventional, non-selective sort (i.e., all modalities affected). The curve labelled TW shows the time course of 4 μg of TTX in the Tween™ 80 carrier used in the capsaicin-containing experiments; the carrier itself did not account for the prolongation seen when capsaicin and TTX are combined.

FIG. 10 is a graph of the effect on hotplate latency, measured as percentage of the maximum effect, of 4 μg of TTX in saline (T4), 4 μg of TTX in a Tween™-containing carrier (TW), 4 μg of TTX with 30 μg of capsaicin (both Cap+T curves), and 0.125% bupivacaine with 30 μg of capsaicin (Cap+B). Noci refers to thermal nociception. n=11 for T4, n=4 for all others.

The combination of 0.125% bupivacaine with 30 μg of capsaicin (Cap+B: Noci) did not prolong thermal nociceptive blockade beyond that of 0.125% % bupivacaine alone. However, a delayed increase in thermal latency was noted after 10 to 12 hours (See FIG. 10; n=4).

FIG. 10 is a graph comparing the effect of 30 μg of capsaicin in 0.125% bupivacaine on thermal nociception (Noci), tactile placing response (TPR; see explanation below), and ability to hop (Hop).

In contrast to the block enhancement seen when TTX and capsaicin are combined, this delayed block was modality-specific. Thermal nociception (Cap+B: Noci) was impaired, while the tactile placing response (TPR, a measure of proprioceptive and motor function), hopping (a complex measure of sensory and motor function), and weight bearing (a measure of motor strength; data not shown) were unimpaired. As seen in FIG. 11, this increase in thermal latency typically lasted 8 to 10 days (C 120 refers to the 120 μg dose of capsaicin used in those experiments together with 0.125% bupivacaine.)

FIG. 11 is a graph of the time course of the effect of 30 μg of capsaicin in 0.125% BPV on thermal nociception (adjusted latency) over a ten-day period. TPR, hopping, and weight-bearing were normal (i.e at baseline) during this period, except as shown in FIG. 11.

Example 7

Effect of Microencapsulation of TTX with or without Epinephrine in Polymer Nicrospheres Poly(lactic acid-glycolic acid, 65:35) microspheres containing a small amount of TTX (0.1% theoretical loading) were prepared. Approximately 30 mg were injected near the sciatic nerve of a rat. The carrier fluid contained 1:100,000 epinephrine to reduce toxicity. The resulting nerve block is shown in FIG. 12. In this and the subsequent figures, the Y-axis displays adjusted latency (labelled as “Latency” in FIG. 12). This is the length of time a rat will leave his foot on a 56° C. hotplate, minus 2 seconds (baseline) It is a measure of the degree of nerve blockade (10=maximal block, 0=no block; 5 seconds is considered the cutoff for effective block). The block had onset in a little more than one hour, and lasted about six hours, with no evidence of systemic toxicity.

Example 8

Effect of Addition of TTX to Bupivacaine Containing Microspheres

TTX (0.2% theoretical loading) was combined with 50% by weight bupivacaine in poly(lactic acid-glycolic acid, 65:35) microspheres. Three rats were given sciatic nerve blocks with 80 mg of these microspheres. The carrier fluid contained 1:100,000 epinephrine to reduce toxicity. The results are shown in FIG. 13. The duration of effective block (i.e. adjusted latency greater han or equal to 5, 50% block) was almost 3 days. This represents a dramatic improvement over microspheres which contain bupivacaine alone, which typically yield a block lasting less than 12 hours.

Example 9

Effect of Addition of Dexamethasone to TTX and Bupivacaine Containing Microspheres TTX (0.2% theoretical loading) was combined with 50% by weight bupivacaine and 0.05% dexamethasone in poly (lactic acid-glycolic acid, 65:35) microspheres. Four rats were given sciatic nerve blocks with 80 mg of these microspheres. The carrier fluid contained 1:100,000 epinephrine to reduce toxicity. The results are shown in FIG. 14. Two rats (1 and 2) had nerve blockade lasting 3.5 to 4.5 days, one lasted 7.5 days, and one lasted almost 13 days. The average duration of effective block (i.e. adjusted latency greater than or equal to 5, 50% block) was 7 days. This represents a great improvement over bupivacaine-dexamethasone microspheres, which typically last 3 to 5 days.

We claim:

1. A composition for causing nerve blockade wherein the nerve blocking agent consists of a site 1 sodium channel blocker in combination with an agent selected from the group consisting of vasoconstrictors, adrenergic drugs, vanilloids, amphiphilic solvents, lipophilic solvents, glucocorticoids, and controlled or prolonged release formulations, wherein the combination is effective to provide prolonged or modality selective nerve blockade in the absence of systemic toxicity.

2. The composition of claim 1 wherein the site 1 sodium channel blockers is selected from the group consisting of tetrodotoxin, saxitoxin, decarbamoyl saxitoxin, neosaxitoxin, and gonyautoxins.

3. The composition of claim 1 wherein the adrenergic drug is selected from the group consisting of alpha agonists, beta-blockers, and mixed central-peripheral alpha-2 agonists.

4. The composition of claim 3 wheren the adrenergic drug is selected from the group consisting of epinephrine, phenylephrine, propranalol, and clonidine.

5. The composition of claim 1 wherein the vanilloid is selected from the group consisting of trans-8-methyl-N-vanillyl-6-nonenamide, N-vanillyl-nonanamide, beta-aminoethyl-substituted phenyl alkanamides, methylene substituted-N-phenylmethyl alkanamides, N-[(substituted phenyl)methyl]-cis-monounsaturated alkenamides, beta-aminoethyl-substituted phenyl compounds, N-[(substituted phenyl)methyl]diunsaturated amides, resinifera compounds, and derivatives and salts thereof.

6. A method for reversing nerve blockade by a vanilloid comprising administering an effective amount of a vanilloid antagonist.

7. A composition for causing nerve blockade wherein the nerve blocking agents consist of a site 1 sodium channel blocker in combination with an enantiomer of local anesthetic effective to prolong nerve blockade as compared to the racemic mixture alone in the absence of systemic toxicity.

8. The composition of claim 1 wherein the glucocorticoid is selected from the group consisting of dexamethasone, cortisone, hydrocortisone, prednisone, beclomethasone, betamethasone, flunisolide, methyl prednisone, para methasone, prednisolone, triamcinolome, alclometasone, amcinonide, clobetasol, fludrocortisone, diflurosone diacetate, fluocinolone acetonide, fluoromethalone, flurandrenolide, halcinonide, medrysone, mometasone, and pharmaceutically acceptable salts and mixtures thereof.

9. The composition of claim 1 wherein the amphiphilic vehicle is selected from the group consisting of non-ionic detergents and alcohols.

10. The composition of claim 1 wherein the amphiphilic vehicle is selected from the group consisting of alcohols, polyoxyethylene sorbitan derivatives, and dimethylsulfoxide.

11. A composition for prolonged nerve blockade comprising a site I channel blocker, wherein the site I channel blocker is in a controlled release formulation.

12. The composition of claim 11 wherein the controlled release formulation is a polymeric carrier selected from the group consisting of microcapsules, microparticles, microspheres, slabs, beads, pellets, pastes, gels and suspensions.

13. The composition of claim 11 wherein the polymeric carrier is in the form of microparticles.

14. The composition of claim 1 wherein the composition provides nerve blockade over a period of time of weeks to months.

15. The composition of claim 7 comprising a site 1 channel blocker in combination with an enantiomer of a local anesthetic formulated to provide prolonged continuous spinal or epidural anesthesia.

16. The method of claim 6 wherein the antagonist is capsazepine.

17. A method for nerve blockade comprising administering to a patient in need thereof an effective amount of a composition selected from the group consisting of compositions for causing nerve blockade wherein the nerve blocking agent consists of a site 1 sodium channel blocker in combination with an agent selected from the group consisting of vasoconstrictors, adrenergic drugs, vanilloids, amphiphilic solvents, lipophilic solvents, glucocorticoids, and controlled or prolonged release formulations, wherein the combination is effective to provide prolonged or modality selective nerve blockade in the absence of systemic toxicity, and compositions wherein the nerve blocking agent consists of a site 1 sodium channel blocker in combination with an enatiomer of local anesthetic, wherein the combination is effective to prolong nerve blockade as compared to the racemic mixture alone, in the absence of systemic toxicity.

18. A method for nerve blockade comprising administering to a patient in need thereof an effective amount of composition comprising a tetrodotoxin wherein the composition is administered to provide spinal or epidural anesthesia.

19. The method of claim 17 wherein the composition is administered to provide management of cancer pain or chronic pain.

20. A method for nerve blockade comprising administering to a patient in need thereof an effective amount of composition comprising a tetrodotoxin wherein the composition is administered to provide an intercostal blockade.

21. A method for nerve blockade comprising administering to a patient in need thereof an effective amount of composition comprising a tetrodotoxin wherein the composition is administered to provide a sympathetic blockade.

22. A method for providing modality specific nerve blockade comprising administering an effective amount of a site I channel blocker.

23. The method of claim 22 wherein the site I channel blocker is a composition selected from the group consisting of compositions for causing nerve blockade wherein the nerve blocking agent consists of a site 1 sodium channel blocker in combination with an agent selected from the group consisting of vasoconstrictors, adrenergic drugs, vanilloids, amphiphilic solvents, lipophilic solvents, glucocorticoids, and controlled or prolonged release formulations, wherein the combination is effective to provide prolonged or modality selective nerve blockade in the absence of systemic toxicity, and compositions wherein the nerve blocking agent consists of a site 1 sodium channel blocker in combination with an enatiomer of local anesthetic, wherein the combination is effective to prolong nerve blockade as compared to the racemic mixture alone, in the absence of systemic toxicity.

* * * * *